United States Patent
Hurkens et al.

(10) Patent No.: US 10,058,498 B2
(45) Date of Patent: Aug. 28, 2018

(54) COMPOSITION AND METHOD OF PRODUCING PERSONAL CARE COMPOSITIONS WITH IMPROVED DEPOSITION PROPERTIES

(71) Applicant: Hercules Incorporated, Wilmington, DE (US)

(72) Inventors: Stephen Hugo Hurkens, Dordrecht (NL); Gijsbert Kroon, Hardinxveld Giessendam (NL); Thi Hong Lan Le-Pham, Voorburg (NL)

(73) Assignee: Hercules LLC, Wilmington, DE (US)

( * ) Notice: Subject to any disclaimer, the term of this patent is extended or adjusted under 35 U.S.C. 154(b) by 37 days.

(21) Appl. No.: 14/881,584

(22) Filed: Oct. 13, 2015

(65) Prior Publication Data

US 2016/0113854 A1  Apr. 28, 2016

Related U.S. Application Data

(63) Continuation of application No. 13/833,330, filed on Mar. 15, 2013.

(51) Int. Cl.

| | | |
|---|---|---|
| *A61K 8/73* | (2006.01) | |
| *A61Q 5/12* | (2006.01) | |
| *A61Q 15/00* | (2006.01) | |
| *A61Q 17/04* | (2006.01) | |
| *A61Q 19/00* | (2006.01) | |
| *A61Q 19/10* | (2006.01) | |
| *A61Q 5/02* | (2006.01) | |
| *C11D 3/22* | (2006.01) | |
| *A61K 8/41* | (2006.01) | |
| *A61K 8/46* | (2006.01) | |
| *C11D 1/12* | (2006.01) | |
| *C11D 1/62* | (2006.01) | |
| *A61K 8/34* | (2006.01) | |
| *A61K 8/36* | (2006.01) | |
| *A61K 8/37* | (2006.01) | |
| *A61K 8/49* | (2006.01) | |
| *A61K 8/63* | (2006.01) | |
| *A61K 8/86* | (2006.01) | |
| *C11D 17/00* | (2006.01) | |

(52) U.S. Cl.
CPC .............. *A61K 8/731* (2013.01); *A61K 8/342* (2013.01); *A61K 8/361* (2013.01); *A61K 8/37* (2013.01); *A61K 8/375* (2013.01); *A61K 8/416* (2013.01); *A61K 8/463* (2013.01); *A61K 8/466* (2013.01); *A61K 8/4946* (2013.01); *A61K 8/63* (2013.01); *A61K 8/86* (2013.01); *A61Q 5/02* (2013.01); *A61Q 5/12* (2013.01); *A61Q 15/00* (2013.01); *A61Q 17/04* (2013.01); *A61Q 19/00* (2013.01); *A61Q 19/10* (2013.01); *C11D 1/123* (2013.01); *C11D 1/62* (2013.01); *C11D 3/222* (2013.01); *C11D 3/225* (2013.01); *C11D 17/0013* (2013.01); *C11D 17/0017* (2013.01); *A61K 2800/10* (2013.01); *A61K 2800/30* (2013.01); *A61K 2800/49* (2013.01); *A61K 2800/524* (2013.01); *A61K 2800/5422* (2013.01); *A61K 2800/596* (2013.01); *A61K 2800/874* (2013.01)

(58) Field of Classification Search
None
See application file for complete search history.

(56) References Cited

U.S. PATENT DOCUMENTS

| | | |
|---|---|---|
| 4,228,277 A | 10/1980 | Landoll |
| 4,243,802 A | 1/1981 | Landoll |
| 4,352,916 A | 10/1982 | Landoll |
| 4,845,207 A | 7/1989 | t'Sas |
| 4,870,167 A | 9/1989 | Zody et al. |
| 4,892,589 A | 1/1990 | Kirkland et al. |
| 4,902,499 A | 2/1990 | Bolish, Jr. et al. |
| 4,939,192 A | 7/1990 | t'Sas |
| 4,960,876 A | 10/1990 | Molteni et al. |
| 5,100,658 A | 3/1992 | Bolich, Jr. et al. |
| 5,104,646 A | 4/1992 | Bolich, Jr. et al. |
| 5,106,609 A | 4/1992 | Bolich, Jr. et al. |
| 5,422,280 A | 6/1995 | Helliwell et al. |

(Continued)

FOREIGN PATENT DOCUMENTS

| | | |
|---|---|---|
| WO | WO/2006/065848 | 6/2006 |
| WO | WO2010130776 | * 11/2010 |

OTHER PUBLICATIONS

SAAPedia, PPG Hydroxyethyl Cocamide, retrieved online on Oct. 15, 2014, http://www.saapedia.org/en/saa/?type=detail&id=3183.*
PCT/US2013/031974—WO/2014/149019—International Search Report and Written Opinion—dated Jun. 2, 2014.
PCT/US2013/031974—WO/2014/149019—International Preliminary Report on Patentability—dated Sep. 24, 2015.

*Primary Examiner* — Jennifer A Berrios
(74) *Attorney, Agent, or Firm* — Dunlap Codding, P.C.; Shaorong Chen

(57) ABSTRACT

The presently disclosed and/or claimed inventive concept(s) relates generally to the use of nonionic hydrophobically modified polysaccharides in personal care and household care compositions. More specifically, but not by way of limitation, the presently disclosed and/or claimed inventive concept(s) relates to the use of hydrophobically-modified cellulose ethers, such as hydrophobically-modified hydroxyethylcellulose (HMHEC) polymers in personal care and household care compositions. These compositions show pronounced syneresis in aqueous solutions or in the presence of surfactants, including nonionic surfactants and anionic surfactants such as lauryl sulfate (LS) and lauryl ether sulfate (LES). It is also contemplated that the surfactants used in the compositions be sulfate free and/or multi-tailed.

18 Claims, No Drawings

(56) References Cited

U.S. PATENT DOCUMENTS

| | | | |
|---|---|---|---|
| 5,512,091 A | 4/1996 | Steiner | |
| 5,855,878 A | 1/1999 | Coffindaffer et al. | |
| 5,877,187 A * | 3/1999 | Orjales | C07D 401/04 |
| | | | 514/322 |
| 5,939,059 A | 8/1999 | Franklin et al. | |
| 6,074,996 A | 6/2000 | Elliott et al. | |
| 6,191,083 B1 | 2/2001 | Brooks et al. | |
| 6,284,230 B1 | 9/2001 | Sako et al. | |
| 6,387,855 B1 | 5/2002 | De La Mettrie | |
| 6,589,517 B1 | 7/2003 | McKelvey et al. | |
| 6,905,694 B1 | 6/2005 | Modi | |
| 7,470,651 B2 | 12/2008 | Uehara et al. | |
| 8,008,239 B2 * | 8/2011 | Anantaneni | A61K 8/466 |
| | | | 510/127 |
| 2001/0043912 A1 | 11/2001 | Michael | |
| 2004/0076595 A1 | 4/2004 | Khan | |
| 2005/0075255 A1 * | 4/2005 | McAtee | A61K 8/0208 |
| | | | 510/122 |
| 2006/0134047 A1 | 6/2006 | Bakeev et al. | |
| 2011/0139170 A1 * | 6/2011 | Hippe | A61K 8/44 |
| | | | 132/202 |
| 2013/0089587 A1 | 4/2013 | Staudigel et al. | |

* cited by examiner

COMPOSITION AND METHOD OF PRODUCING PERSONAL CARE COMPOSITIONS WITH IMPROVED DEPOSITION PROPERTIES

CROSS REFERENCE TO RELATED APPLICATIONS/INCORPORATION BY REFERENCE STATEMENT

The present application is a continuation of U.S. application Ser. No. 13/833,330, filed Mar. 15, 2013. The entirety of which is hereby expressly incorporated herein by reference.

BACKGROUND OF THE INVENTION

1. Field of the Disclosed and Claimed Inventive Concepts

The presently disclosed and/or claimed inventive concept(s) relates generally to the use of nonionic hydrophobically modified polysaccharides in personal care and household care compositions. More specifically, but not by way of limitation, the presently disclosed and/or claimed inventive concept(s) relates to the use of hydrophobically-modified cellulose ethers, such as hydrophobically-modified hydroxyethylcellulose (HMHEC) polymers in personal care and household care compositions. These compositions show pronounced syneresis in aqueous solutions or in the presence of surfactants, including nonionic surfactants and anionic surfactants such as lauryl sulfate (LS) and lauryl ether sulfate (LES). It is also contemplated that the surfactants used in the compositions be sulfate free and/or multi-tailed.

2. Background

In the prior art, the commonly used approach to deliver a polymer coating from personal care or household compositions is through the use of complex formations between cationic polymers and anionic surfactants. It is well-known that for hair care, cleansing skin care, and fabric care applications, the conditioning mechanism for polymers with cationic functionality is based on dilution deposition of a cationic polymer-anionic surfactant complex, referred to as a coacervate complex, which has both a cationic polymer and an oppositely charged surfactant. (U.S. Pat. No. 5,422,280). As a result of this mechanism, commercial products such as cationic guars, cationic hydroxyethylcellulose, and synthetic cationic polymers show high efficacy in conditioning shampoos, skin care cleansing formulations, and fabric cleansing/conditioning formulations.

In personal care applications, such as in hair care and skin care, and in household care applications, there is a desire to deposit a coating onto the substrate (e.g., hair, skin, fabric, etc.) that reduces the energy needed to move a comb through the hair in the wet or dry state or delivers a silky, soft feel to the skin or fabric. This coating can also act to improve the luster and moisture retention of the hair and skin, as well as their manageability and feel.

The discovery of the improved deposition of silicone resins from cleansing formulations, such as shampoos, using cationic polymer-anionic surfactant complexes has led to the development of this approach to condition hair, skin, and fabric. However, the tendency for silicone to buildup on the hair after repeated washings with silicone shampoos, and the desire for clear conditioning formulations has left a strong market need for alternative approaches to achieve silicone-like conditioning on hair, skin, and fabric substrates with or without silicone resins.

Additionally, conditioners containing cationic polymers, with or without silicones/emollients, can irritate skin and are considered to be harmful to the environment despite providing good cleansing and detangling properties for hair. Unfortunately, attempts at replacing the cationic polymers in these compositions have been found lacking in terms of their ability to confer significant and predictable conditioning to keratin substrates as compared to the environmentally harmful, cationically charged polymers. As such, a need remains in the industry to provide an environmentally friendly conditioner capable of providing the same or better conditioning performances as those containing cationic polymers but with less aqua toxicity (i.e., less environmentally harmful water soluble or waterborne components) and less skin irritancy.

Furthermore, there is an underlying need for compositions having an improved overall conditioning performance combined with other desirable attributes such as improved hair volume and manageability, hair repair, hair color retention, skin moisturization and moisture retention, fragrance retention, sunscreen longevity on hair, skin, and fabrics, flavor enhancement and antimicrobial performance in oral care applications, and fabric abrasion resistance and colorfastness in household applications.

Prior to the presently disclosed and/or claimed inventive concept(s) invention, water soluble polysaccharides have been used in personal care applications, such as cleansing and cosmetic skin care, hair care, and oral care applications, and in household applications such as cleaning, sanitizing, polishing, toilet preparations, and pesticide preparations. Water soluble polysaccharides have additionally been used in applications such as air deodorants/fresheners, rug and upholstery shampoos, insect repellent lotions, all purpose kitchen cleaner and disinfectants, toilet bowl cleaners, fabric softener-detergent combinations, fabric softeners, fabric sizing agents, dishwashing detergents, and vehicle cleaners and shampoos. Widely used commercially available polysaccharides include water soluble polysaccharide ethers such as methyl cellulose (MC), hydroxypropylmethylcellulose (HPMC), hydroxyethylcellulose (HEC), hydroxypropylcellulose (HPC), ethylhydroxyethylcellulose (EHEC), hydroxypropyl (HP) guar, hydroxyethyl guar, guar, starch, and other nonionic starch and guar derivatives.

U.S. Pat. Nos. 5,106,609, 5,104,646, 6,905,694, and 5,100,658 are examples of patents that disclose the use of hydrophobically modified cellulose ethers in cosmetic products. These patents disclose the use of high weight average molecular weight (i.e., 300,000 to 700,000) and alkyl carbon substitution in the hydrophobe (i.e., 3 to 24 carbons) for use in cosmetic compositions. U.S. Pat. No. 4,243,802 discloses a hydrophobically modified nonionic, water-insoluble, surfactant-soluble cellulose ether composition. The use of this material to increase the viscosity of an acidic shampoo composition and to emulsify oil in water emulsions is mentioned. Also, U.S. Pat. Nos. 4,228,277 and 4,352,916 describe hydrophobically modified cellulose ether derivatives modified with long chain alkyl group substitution in the hydrophobe. U.S. Pat. No. 5,512,091 discloses hydrogel compositions containing water-insoluble hydrophobically modified cellulose ethers. Publication US2001/0043912 discloses anti-frizz hair care compositions containing a hydrophobically modified cellulose ether thickener. U.S. Pat. No. 4,845,207 discloses a hydrophobically modified nonionic, water-soluble cellulose ether and U.S. Pat. No. 4,939,192 discloses the use of such ether in building compositions. U.S. Pat. No. 4,960,876 discloses hydrophobically modified galactomannan compositions as thickeners for use in paint, paper, and ceramic applications. U.S. Pat. No. 4,870,167 discloses hydrophobically modified nonionic polygalactomannan ethers prepared from long-chain aliphatic epoxides, and suggests their possible use in cosmetics, including hand lotions, shampoos, hair treatment compounds, toothpastes, and gels for cleaning teeth. U.S. Pat. No. 6,387,855 discloses aqueous compositions containing silicone, a surfactant, and a hydrophobic galactomannan gum for washing and conditioning keratin.

Additionally, U.S. Pat. Nos. 6,284,230 and 7,470,651 and Publication No. 2006/0293197 disclose the deposition of active ingredients to hair through the well-known process of forming a coacervate complex. U.S. Pat. No. 4,892,589 discloses the combination of water-soluble, nonionic hydrophobically modified hydroxyethylcellulose and water-soluble, nonionic hydroxyethylcellulose composition used for cement. U.S. Pat. No. 4,902,499 discloses a hair care composition containing a rigid silicone polymer, and U.S. Publication No. 2004/0076595 discloses a hair care composition containing a cationic thickener, nonionic thickener, or mixtures thereof, and at least one cationic surfactant, wherein the composition preferably also contains a silicone compound. U.S. Pat. No. 6,589,517 discloses a leave on conditioner, i.e., a hair conditioner that is intended to be used without a rinsing step. U.S. Pat. Nos. 6,074,996 and 6,191,083 disclose the use of cationic polymeric agents. Also, U.S. Pat. No. 5,855,878 discloses a cosmetic composition containing a hydrophobically modified nonionic polymer and an unsaturated quaternary ammonium surfactant, however, such composition is incapable of providing adequate performance for conditioning hair due to the surfactants claimed therein being incompatible with typical shampoo compositions.

The performance of water-soluble and water-insoluble hydrophobically modified celluloses has been found lacking in terms of their ability to confer significant and predictable conditioning to keratin substrates. Hence, a need still exists in the industry to have cellulose ethers that confer significant and predictable conditioning to keratin substrates and deposit films onto solid substrates, such as fabrics, when delivered from aqueous compositions.

Additionally, nonionic hydrophobically modified polysaccharides have also been found lacking in terms of their ability to confer significant and predictable conditioning to keratin substrates without using environmentally harmful cationically charged polymers. As such, an additional need exists in the industry for a method of utilizing environmentally friendly nonionic cellulose ethers capable of conferring significant and predictable conditioning to keratin substrates, such as hair, when delivered from aqueous compositions.

SUMMARY OF THE INVENTION

The presently disclosed and/or claimed inventive concept(s) is directed to a method of conditioning a functional system substrate, comprising the steps of:
  (a) applying an aqueous solution to a functional system substrate, the aqueous solution comprising: (i) at least one surfactant comprising a multi-tail surfactant, (ii) at least one functional system active ingredient, and (iii) a nonionic hydrophobically modified cellulose ether having a weight average molecular weight of from 100,000 to 2,000,000 and is hydrophobically substituted, wherein the amount of the hydrophobic substitution of the nonionic hydrophobically modified cellulose ether is in a range from a lower limit of 0.8 weight percent to an upper limit rendering the nonionic hydrophobically modified cellulose ether soluble in a five weight percent solution of surfactant, and at least one of (1) less than 0.05 percent by weight soluble in water, and (2) less than 0.05 percent by weight soluble in a one percent surfactant solution; and
  (b) diluting the aqueous solution with water such that the aqueous solution undergoes syneresis, whereby the nonionic hydrophobically modified cellulose ether separates from the aqueous solution and deposits upon the functional system substrate.

Additionally, the presently disclosed and/or claimed inventive concept(s) is directed to an improved method of conditioning a functional system substrate, comprising the steps of:
  (a) applying an aqueous solution to a functional system substrate, the aqueous solution comprising: (i) a surfactant comprising at least one multi-tail surfactant, (ii) at least one functional system active ingredient, and (iii) a nonionic hydrophobically modified cellulose ether having a weight average molecular weight of from 100,000 to 2,000,000, and is hydrophobically substituted, wherein the amount of the hydrophobically modified cellulose is in a range from a lower limit of 0.8 weight percent to an upper limit rendering the nonionic hydrophobically modified cellulose ether soluble in a five weight percent solution of surfactant, and at least one of (1) less than 0.05 percent by weight soluble in water, and (2) less than 0.05 percent by weight soluble in a one percent surfactant solution, and
  (b) diluting the aqueous solution with water such that the aqueous solution undergoes syneresis, whereby the nonionic hydrophobically modified cellulose ether separates from the aqueous solution and deposits upon the functional system substrate.

The presently disclosed and/or claimed inventive concept(s) is further directed to an improved method of conditioning a functional system substrate, comprising the steps of:
  (a) applying an aqueous solution to a functional system substrate, the aqueous solution comprising: (i) a surfactant comprising at least one single tail sulfate-free surfactant, (ii) at least one functional system active ingredient, and (iii) a nonionic hydrophobically modified cellulose ether having a weight average molecular weight of from 100,000 to 2,000,000 and is hydrophobically substituted, wherein the amount of the hydrophobically modified cellulose is in a range from a lower limit of 0.8 weight percent to an upper limit rendering the nonionic hydrophobically modified cellulose ether soluble in a five weight percent solution of surfactant, and at least one of (1) less than 0.05 percent by weight soluble in water, and (2) less than 0.05 percent by weight soluble in a one percent surfactant solution, and
  (b) diluting the aqueous solution with water such that the aqueous solution undergoes syneresis, whereby the nonionic hydrophobically modified cellulose ether separates from the aqueous solution and deposits upon the functional system substrate.

The presently disclosed and/or claimed inventive concept(s) is also directed to a process of conditioning an aqueous based functional system selected from the group consisting of personal care and household care products comprising adding and mixing a sufficient amount of a hydrophobically modified cellulose ether that is compatible with the aqueous based functional system to thicken the functional system wherein the hydrophobically modified cellulose ether is a nonionic hydrophobically modified cellulose ether (HMCE) having a weight average molecular weight (Mw) of from 100,000 to 2,000,000 and is hydrophobically substituted, wherein the amount of the hydrophobic substitution of the nonionic hydrophobically modified cellulose ether is in a range from a lower limit of 0.8 weight percent to an upper limit rendering the nonionic hydrophobically modified cellulose ether soluble in a five weight percent solution of surfactant, and at least one of (1) less than 0.05 percent by weight soluble in water, and (2) less than 0.05 percent by weight soluble in a one percent surfactant solution, and wherein the cellulose ether provides a conditioning benefit to a functional system substrate, and the resulting functional system has comparable or better conditioning properties as compared to when using similar thickening agents outside the scope of the present composition(s) and/or method(s).

The hydrophobically modified polysaccharide polymers of the presently disclosed and/or claimed inventive concept(s) can be either water-soluble with the formation of a homogeneous gel above a certain polymer concentration in water (i.e., the critical concentration) or partially soluble in water (i.e., reaching a solution by dissolving the hydrophobically modified polysaccharide by dissolving with the help of at least one surfactant). In both cases, the significant feature of this polymer is the ability to undergo syneresis when diluted to a concentration below a certain critical polymer concentration. Such polymers are useful as conditioning agents in 2-in-1 shampoos, in body cleansing formulations, in oral care cleansing systems such as dentifrices, and in fabric cleansing-conditioning systems due to their unique mechanism of activity and dilution-deposition upon rinsing.

By syneresis and dilution-deposition, it is meant that the hydrophobically modified polysaccharide, whose original concentration is between 0.05%-10% by weight, undergoes liquid-gel phase separation (i.e., syneresis) in aqueous solutions when diluted to a final concentration with a lower limit of 0.01% by weight in solution. The discussed polymers are water-soluble with the formation of a homogeneous gel above a concentration in water of 0.1%-1%. The significant and unique requirement of these gels is the ability to undergo syneresis upon dilution with water below a certain concentration in the personal care composition. These polymers can be synthesized by methods known in the prior art.

In addition to polymers, the aqueous solution can include surfactant/water mixtures, cyclodextrin/surfactant/water mixtures, water-miscible solvents, salts, water soluble nonionic, cationic, or anionic polymers, and a combination of any of these.

The aqueous solution can also include multi-tail surfactant/water mixtures, cyclodextrin/multi-tail surfactant/water mixtures, water-miscible solvents, salts, water soluble nonionic, cationic, or anionic polymers, and a combination of any of these.

Multi-tail surfactants have been found to improve the conditioning benefits provided by nonionic hydrophobically modified polymer-containing compositions such that they provide similar, if not better, conditioning benefits to substrates than those compositions containing cationic polymers and/or silicones and/or emollients. When combined with at least one multi-tail surfactant in solution, the nonionic hydrophobically modified polysaccharides have been found to interact with the hydrophobic chains, or "tails", of the multi-tail surfactants to form more stable and denser hydrophobic structures on keratin substrates, thereby improving the conditioning benefits provided thereon. For example, the combination of multi-tail surfactants and nonionic hydrophobically modified polysaccharides in shampoo compositions provides similar or better results than their cationic polymer counterparts for both sodium laureth sulfate/cocamidopropyl betain (SLES/CAPB) systems and sulfate-free systems.

DETAILED DESCRIPTION OF THE INVENTION

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those skilled in the art that variations may be applied to the articles and/or methods and in the steps or in the sequence of steps of the method described herein without departing from the concept, spirit, and scope of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one", but it is also consistent with the meaning of "one or more", "at least one", and "one or more than one". The use of the term "or" is used to mean "and/or" unless explicitly indicated to refer to alternatives only if the alternatives are mutually exclusive, although the disclosure supports a definition that refers to only alternatives "and/or". Throughout this application, the term "about" is used to indicate that a value includes the inherent variation of error for the quantifying device, the method being employed to determine the value, or the variation that exists among the study subjects. For example, but not by way of limitation, when the term "about" is utilized, the designation value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABC-CCC, CBBAAA, CABABB, and so forth. The skilled artisan will understand that typically there is no limit on the number of items or terms in any combination, unless otherwise apparent from the context.

It has been found that if a hydrophobically modified polysaccharide polymer undergoes syneresis upon dilution in aqueous solution, the hydrophobically modified polysaccharide polymer can deposit with high efficacy on substrates such as hair, skin, teeth, oral mucosa, or textile fabrics and can impart great conditioning benefits to the substrates. Upon deposition onto the substrate, the hydrophobically modified polysaccharide can also deposit other ingredients which improve the conditioning or enhance the characteristics of the substrate. These polymers also have potential for conditioning skin when used in cleansing or moisturizing formulations, since these polymers may also better deliver the oil phase typically used in such creams and lotions.

Surprisingly, it has been found that nonionic hydrophobically modified polysaccharides, preferably cellulose derivatives, and more specifically hydrophobically modified hydroxyethylcellulose, HMHEC, that show pronounced syneresis in aqueous solution upon dilution can deposit with high efficacy on hair/skin and can impart enhanced conditioning benefits to keratin substrates. Such polymers impart other benefits in hair styling, body lotions, and sunscreens due to hydrophobic film formation on keratin substrates that acts as a barrier between the surfaces and the surrounding atmosphere.

Although it has been found that nonionic hydrophobically modified polysaccharides show pronounced syneresis in aqueous solutions upon dilution and can deposit with relatively high efficacy on substrates, compositions in the prior art containing nonionic hydrophobically modified polysaccharides have been found to have inferior conditioning properties to compositions containing environmentally harmful, but effective, cationic polymers. However, it has been surprisingly found that the addition of at least one multi-tail surfactant improves the conditioning properties of nonionic hydrophobically modified polysaccharide compositions such as to provide similar or better conditioning benefits as the environmentally harmful compositions containing cationic polymers and/or silicones and/or emollients.

Furthermore, it has been found that nonionic hydrophobically modified polysaccharide compositions containing surfactants consisting of only sulfate-free surfactants are capable of showing pronounced syneresis in aqueous solutions upon dilution and can deposit on substrates with a similar or better efficacy than compositions containing cationic polymers, even without the presence of multi-tail surfactants. It has also been found that the addition of multi-tail surfactants to compositions containing both nonionic hydrophobically modified polysaccharide compositions and sulfate-free surfactants does not interfere with the deposition efficacy of the compositions.

Moreover, it has been found that the addition of sodium chloride to nonionic hydrophobically modified polysaccharide compositions containing surfactants consisting of only sulfate-free surfactants further improves the deposition efficacy of such compositions, which thereby results in improved conditioning properties on the substrate. Improvements in deposition efficacy and conditioning properties resulting from the addition of sodium chloride was also found to occur in nonionic hydrophobically modified polysaccharide compositions containing both sulfate-free surfactants and multi-tail surfactants.

Nonionic hydrophobically modified polysaccharides may be useful as film-formers and co-deposition agents onto the surfaces of hair, skin, and textiles, aiding in protection of the hair, skin, and textile substrates from moisture-loss, aiding deposition of sunscreens and subsequent protection of these substrates from UV radiation, enhancing deposition of fragrance or flavor onto substrates and entrapping fragrance and flavor leading to their improved longevity on these substrates, or aiding deposition of antimicrobial reagents and other active personal care ingredients, resulting in improved longevity of the active on the substrate. In addition, these polymers find use in oral care applications such as dentifrices and denture adhesives to deliver prolonged flavor retention and flavor release. Prolonged release of antimicrobial and biocide agents from these polymers may also find usefulness in household and personal care applications, such as skin and hair treatment formulas and in oral care applications such as dentifrice, denture adhesives, and whitening strips.

In accordance with the presently disclosed and/or claimed inventive concept(s), the conditioning benefits of hydrophobically modified polysaccharides, preferably hydrophobically modified cellulose ether polymers, are demonstrated as conditioning agents in personal care compositions such as hair care, skin care, and oral care compositions as well as household care compositions, such as laundry cleaner and softener products for textile substrates and hard surface cleaner products.

In accordance with the presently disclosed and/or claimed inventive concept(s), the functional system substrate is defined as a material that is related to personal care and household care applications. In personal care, the substrate can be skin, hair, teeth, and mucous membranes. In household care products, the substrate can be hard surfaces such as metals, marbles, ceramics, granite, wood, hard plastics, and wall boards or textiles fabrics.

Any water soluble polysaccharide or derivatives can be used as the backbone to form the hydrophobically modified polysaccharide of the presently disclosed and/or claimed inventive concept(s). Thus, e.g., hydroxyethylcellulose (HEC), hydroxypropylcellulose (HPC), methylcellulose (MC), hydroxypropylmethylcellulose (HPMC), ethylhydroxyethylcellulose (EHEC), and methylhydroxyethylcellulose (MHEC) and, agar, dextran, starch, and their nonionic derivatives can all be modified. The amount of nonionic substituent such as methyl, hydroxyethyl, or hydroxypropyl does not appear to be critical so long as there is a sufficient amount to assure that the ether is water soluble. The polysaccharides of the presently disclosed and/or claimed inventive concept(s) have a sufficient degree of nonionic substitution to cause them to be water soluble and a hydrophobic moiety including 1) 3-alkoxy-2-hydroxypropyl group wherein the alkyl moiety is a straight or branched chain having 3-30 carbon atoms, or 2) $C_3$-$C_{30}$ alkyl, and $C_7$-$C_{30}$ aryl, aryl alkyl, and alkyl aryl groups and mixtures thereof, wherein the hydrophobic moiety is present in an amount up to the amount that produces a hydrophobically-modified polysaccharide that shows pronounced syneresis in aqueous solution or in the presence of surfactants such as, for example, lauryl sulfate (LS) and lauryl ether sulfate (LES) surfactants. When the hydrophobe is an alkyl moiety, the number of carbons can be 3-30, preferably 6-22, more preferably 8-18, and most preferably 10-16. The aryl, aryl alkyl, or alkyl aryl moiety can have an upper limit carbon amount of 30 carbons, preferably 22 carbons, more preferably 18 carbons, and even more preferably 16 carbons. The lower limit of the carbon amount is 7 carbons, more preferably 8 carbons, and even more preferably 10 carbons.

The preferred polysaccharide backbone is hydroxyethylcellulose (HEC). The HEC which is modified to function in the presently disclosed and/or claimed inventive concept(s) is a commercially available material. Suitable commercially available materials are marketed by the Aqualon Company, a division of Hercules, Incorporated, Wilmington, Del. U.S.A., under the trademark NATROSOL®.

The alkyl modifier can be attached to the polysaccharide backbone via an ether, ester, or urethane linkage. Ether is the preferred linkage as the reagents most commonly used to effect etherification because it is readily obtainable. The reaction is similar to that commonly used for the initial etherification, and the reagents used in the reaction are usually more easily handled than the reagents used for modification via the other linkages. The resulting linkage is also usually more resistant to further reactions.

An example of one polysaccharide of the presently disclosed and/or claimed inventive concept(s) is the 3-alkoxy-2-hydroxypropylhydroxyethylcellulose that shows pronounced syneresis in aqueous solution or in the presence of nonionic surfactants, such as acetylene based surfactants, or in the presence of anionic surfactants such as, for example, lauryl sulfate (LS) and lauryl ether sulfate (LES) surfactants.

The hydrophobic moiety is generally contained in an amount such that the hydrophobic substitution of the hydrophobically modified cellulose ether is in a range from a lower limit of 0.8 weight percent to an upper limit rendering the nonionic hydrophobically modified polysaccharide cellulose ether soluble in a five weight percent solution of surfactant, and at least one of (1) less than 0.05 percent by weight soluble in water, and (2) less than 0.05 percent by weight soluble in a one percent surfactant solution. The alkyl group of the 3-alkoxy-2-hydroxypropyl group can be a straight or branched chain alkyl group having 3 to 30 carbon atoms. Exemplary modifying radicals are propyl-, butyl-, pentyl-, 2-ethylhexyl, octyl, cetyl, octadecyl, methylphenyl, and docosapolyenoic glycidyl ether.

While the hydrophobically modified polysaccharide of the presently disclosed and/or claimed inventive concept(s) is the backbone ingredient of the system, an optional ingredient that may be in the system is a surfactant that can be either single tail or multi-tail and either soluble or insoluble in the composition. Another optional ingredient that may be used in the system is a compatible solvent that can be either a single solvent or a blend of solvents.

Examples of surfactants useful with the presently disclosed and/or claimed inventive concept(s) are anionic, nonionic, cationic, zwitterionic, or amphoteric type of surfactants, and combinations thereof. Except for cationic surfactants, the surfactant can be soluble or insoluble in the presently disclosed and/or claimed inventive concept(s) and, when used, is present in the composition in the amount of from 0.01 to about 50 wt % by weight of the composition. Synthetic anionic surfactants include alkyl and alkyl ether sulfates. Cationic surfactants can be present in an amount of from 0.01 to about 1.0 wt %. Further examples of the surfactants include single tail surfactants, multi-tail surfactants, and combinations thereof.

Single tail surfactants are broadly defined as anionic, nonionic, cationic, zwitterionic, or amphoteric types of surfactants, and combinations thereof, having only a single hydrocarbon (i.e., alkyl) chain. The hydrocarbon chain can be straight or branched and can have one or more moieties on the hydrocarbon chain comprising a solvophobic group (i.e., lacking an affinity for a specific solvent, for example, water) and/or a solvophilic group (i.e., having an affinity for a specific solvent). Examples of single tail surfactants are sodium lauryl sulfate, sodium laureth sulfate, cocamidopropyl betain, oleth-5 phosphate, sodium lauroyl sarcosinate, sodium lauroamphoacetate, and decyl glucoside.

Multi-tail surfactants are broadly defined as anionic, cationic, zwitterionic, or amphoteric types of surfactants, and combinations thereof, having more than one hydrocarbon (i.e., alkyl) chain. The at least two hydrocarbon chains can be straight, branched, or aromatic and can have one or more moieties on the hydrocarbon chains comprising a solvophobic group (i.e., lacking an affinity for a specific solvent, for example, water) and/or a solvophilic group (i.e., having an affinity for a specific non-polar or low polar solvent). More specifically, but not by way of limitation, the hydrocarbon chains of the multi-tail surfactants are preferably hydrophobic in the presently disclosed and/or claimed inventive concept(s) so as to form more stable and denser hydrophobic structures on the substrate. When combined with at least one multi-tail surfactant in solution, the nonionic hydrophobically modified polysaccharides have been found to interact with the hydrophobic chains, or "tails", of the multi-tail surfactants to form more stable and denser hydrophobic structures on keratin substrates, thereby improving the conditioning benefits provided thereon. These hydrophobic structures improve the conditioning capabilities of the nonionic hydrophobically modified polysaccharide compositions, with or without active ingredients optionally contained therein. Examples of multi-tail surfactants include, but are not limited to, dioctyl sulfosuccinates like sodium dioctyl sulphosuccinate, and quaternary ammonium compounds with long alkyl chains like dicoco dimethylammonium chloride, dipalmitoylethyl hydroxyethylmonium methosulfate, and dialkyl ammonium methosulfate. Multi-tail surfactants such as those marketed under the trade names STEPANTEX® DC 90 (Stepan Company, Northfield, Ill.), STEPANQUAT® GA-90 (Stepan Company, Northfield, Ill.), ARQUAT® 2C-75 (AkzoNobel, Chicago, Ill.) and AEROSOL® OT (Cytec Industries Inc., West Paterson, N.J.) are also useful in the presently disclosed and/or claimed inventive concept(s).

Nonionic surfactants can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Nonionic surfactants such as those marketed under the trade name SURFYNOL® (Air Products and Chemicals, Inc., Allentown, Pa.) are also useful in the presently disclosed and/or claimed inventive concept(s). Cationic surfactants useful in vehicle systems of the compositions of the presently disclosed and/or claimed inventive concept(s) contain amino or quaternary ammonium hydrophilic moieties which are positively charged when dissolved in the disclosed aqueous composition. Zwitterionic surfactants are exemplified by those which can be broadly described as derivatives of aliphatic quaternary ammonium, phosphonium, and sulfonium compounds, which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. Examples of amphoteric surfactants which can be used in the disclosed systems and compositions are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Sulfate-free surfactants can be broadly defined as either single tail or multi-tail surfactants, or combinations thereof, that are generally free from salts or esters of sulfuric acid. Examples of sulfate-free surfactants include, but are not limited to, sodium lauroyl sarcosinate, sodium lauroamphoacetate, cocamidopropyl betain, and decyl glucoside.

According to the presently disclosed and/or claimed inventive concept(s), the solvent used in the system should be compatible with the other components of the disclosed compositions. Examples of the solvents that may be used are water, water-lower alkanols mixtures, and polyhydric alcohols having from 3 to 6 carbon atoms and from 2 to 6 hydroxyl groups. Preferred solvents are water, propylene glycol, water-glycerine, sorbitol-water, and water-ethanol. The solvent, when used, is present in the composition at a level of from 0.1% to 99% by weight of the composition.

In certain instances, the active component is optional because the dissolved polymer can be the active ingredient component. An example of this is the use of the polymer in a conditioner formulation for hair or skin conditioning or in a fabric conditioner formulation. However, when an active ingredient is needed, it should provide some benefit to the user, the user's body, and/or the substrate to which it is applied.

In accordance with the presently disclosed and/or claimed inventive concept(s), the functional system may be either a personal care product or a household care product. When the functional system is a personal care product that contains at least one active personal care ingredient, the personal care active ingredient includes, but is not limited to, analgesics, anesthetics, antibiotic agents, antifungal agents, antiseptic agents, antidandruff agents, antibacterial agents, vitamins, hormones, antidiarrhea agents, corticosteroids, anti-inflammatory agents, vasodilators, kerolytic agents, dry-eye compositions, wound-healing agents, anti-infection agents, as well as solvents, diluents, adjuvants and other ingredients such as water, ethyl alcohol, isopropyl alcohol, propylene glycol, higher alcohols, glycerine, sorbitol, mineral oil, preservatives, surfactants, propellants, fragrances, essential oils, and viscosifying agents.

Personal care compositions include hair care, skin care, sun care, nail care, and oral care compositions. Examples of active substances that may suitably be included, but not limited to, in the personal care products according to the presently disclosed and/or claimed inventive concept(s) are as follows: 1) Perfumes, which give rise to an olfactory response in the form of a fragrance and deodorant perfumes which in addition to providing a fragrance response can also reduce body malodor; 2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin; 3) Emollients, such as isopropylmyristate, silicone materials, mineral oils and vegetable oils which give rise to a tactile response in the form of an increase in skin lubricity; 4) Deodorants other than perfumes, whose function is to reduce the level of or eliminate micro flora at the skin surface, especially those responsible for the development of body malodor. Precursors of deodorants other than perfume can also be used; 5) antiperspirant actives, whose function is to reduce or eliminate the appearance of perspiration at the skin surface; 6) moisturizing agents, that keep the skin moist by either adding moisture or preventing from evaporating from the skin; 7) cleansing agents, that remove dirt and oil from the skin; 8) sunscreen active ingredients that protect the skin and hair from UV and other harmful light rays from the sun. In accordance with this invention, a therapeutically effective amount will normally be from 0.01 to 10% by weight, preferable 0.1 to 5% by weight of the composition; 9) hair treatment agents that condition hair, cleanse hair, detangle hair, act as styling agents, volumizing and gloss agents, color retention agents, antidandruff agents, hair growth promoters, hair dyes and pigments, hair perfumes, hair relaxer, hair bleaching agents, hair moisturizer, hair oil treatment agents, and antifrizzing agents; 10) oral care agents, such as dentifrices and mouth washes that clean, whiten, deodorize and protect the teeth and gum; 11) denture adhesives that provide adhesion properties to dentures; 12) shaving products such as creams, gels and lotions and razor blade lubricating strips; 13) tissue paper products such as moisturizing or cleansing tissues; 14) beauty aids such as foundation powders, lipsticks, and eye care; and 15) textile products such as moisturizing or cleansing wipes.

In accordance with the presently disclosed and/or claimed inventive concept(s), when the functional system is a household care composition, this household care product includes a hydrophobically modified polysaccharide and at least one active household care ingredient. The household care active ingredient should provide some benefit to the user. Examples of active substances that may suitably be included, but not limited to, according to the present invention are as follows: 1) perfumes, which give rise to an olfactory response in the form of a fragrance and deodorant perfumes which in addition to providing a fragrance response can also reduce odor; 2) insect repellent agent whose function is to keep insects from a particular area or attacking skin; 3) bubble generating agent such as surfactant that generates foam or lather; 4) pet deodorizer or insecticides such as pyrethrins that reduce pet odor; 5) pet shampoo agents and actives, whose function is to remove dirt, foreign material and germs from the skin and hair surfaces; 6) industrial grade bar, shower gel, and liquid soap actives that remove germs, dirt, grease and oil from skin, sanitizes skin, and conditions the skin; 7) all purpose cleaning agents that remove dirt, oil, grease, and germs from the surface in areas such as kitchens, bathroom, and public facilities; 8) disinfecting ingredients that kill or prevent growth of germs in a house or public facility; 9) rug and upholstery cleaning actives which lift and remove dirt and foreign particles from the surfaces and also deliver softening and perfumes; 10) a laundry softener active which reduces static and makes fabric feel softer; 11) laundry detergent ingredients which remove dirt, oil, grease, stains and kills germs; 12) laundry or detergent or fabric softener ingredients that reduce color loss during the wash, rinse, and drying cycle of fabric care; 13) dishwashing detergents which remove stains, food, germs; 14) toilet bowl cleaning agents which remove stains, kills germs, and deodorizes; 15) laundry prespotter actives which help in removing stains from clothes; 16) fabric sizing agents which enhance appearance of fabric; 17) vehicle cleaning actives which removes dirt, grease, etc., from vehicles and equipment; 18) lubricating agents which reduce friction between parts; and 19) textile products such as dusting or disinfecting wipes.

The above enumerated personal care and household care active ingredients are only examples and are not complete lists of active ingredients that can be used. Other ingredients that are used in these types of products are well known in the industry and would be apparent to one of ordinary skill in the art given the present disclosure. In addition to the above ingredients conventionally used, compositions according to the presently disclosed and/or claimed inventive concept(s) can optionally also include ingredients such as a colorant, preservative, antioxidant, nutritional supplements, alpha or beta hydroxy acid, activity enhancer, emulsifiers, functional polymers, viscosifying agents (such as salts, i.e., NaCl, $NH_4Cl$, and KCl, water-soluble polymers, i.e., hydroxyethylcellulose and hydroxypropylmethylcellulose, and fatty alcohols, i.e., cetyl alcohol), alcohols having 1-6 carbons, fats or fatty compounds, antimicrobial compound, zinc pyrithione, silicone material, hydrocarbon polymer, emollients, oils, surfactants, medicaments, flavors, fragrances, suspending agents, and mixtures thereof.

In accordance with the presently disclosed and/or claimed inventive concept(s), examples of functional polymers that can be used in blends with the hydrophobically modified polysaccharides or derivatives thereof used herein include water-soluble polymers such as acrylic acid homopolymers such as CARBOPOL® (Lubrizol Advanced Materials, Inc., Cleveland, Ohio) products and anionic and amphoteric acrylic acid copolymers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; acrylamide homopolymers and cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and nonionic, anionic, hydrophobic, amphoteric, and cationic polysaccharides such as xanthan, chitosan, carboxymethyl guar, alginates, gum arabic, hydroxypropyl guar, hydrophobic guar polymers, carboxymethyl guar hydroxypropyltrimethylammonium chloride, guar hydroxypropyltrimethylammonium chloride, and hydroxypropyl guar hydroxypropyltrimethylammonium chloride.

In accordance with the presently disclosed and/or claimed inventive concept(s), the silicone materials which can be used are polyorganosiloxanes that can be in the form of polymers, oligomers, oils, waxes, resins, or gums or polyorganosiloxane polyether copolyols, amodimethicones, cationic polydimethylsiloxane materials and any other silicone material that is used in personal care or household compositions.

The polymers of the presently disclosed and/or claimed inventive concept(s) are water-soluble with the formation of a homogeneous gel above a certain concentration in water of 0.01%-1%. These gels undergo syneresis upon dilution below certain concentrations in the personal care composition. These polymers can be synthesized by methods known in the prior art.

Other water-insoluble HMHECs that form gels or solutions in surfactant/water or ethanol/water mixtures, and undergo syneresis upon dilution below certain concentrations in the personal care composition are also useful. The polymers of this invention can be useful as conditioning agents in 2-in-1 shampoos, body lotions, sunscreens, anti-frizz, and hair styling. The polymers of the presently disclosed and/or claimed inventive concept(s) can also be used to improve hair volume, manageability, hair repair or color retention, skin moisturization and moisture retention, fragrance retention, sunscreen longevity on hair, skin, and fabrics, flavor enhancement and antimicrobial performance in oral care applications, and improve fabric abrasion resistance and colorfastness in household applications.

For a more detailed understanding of the presently disclosed and/or claimed inventive concept(s), reference can be made to the following examples which are intended as further illustrations of the presently disclosed and/or claimed inventive concept(s) but are not to be construed in a limiting sense. All parts and percentages are by weight unless stated otherwise.

EXAMPLES

Wet and dry hair comb ability measurements are typical test methods used to measure conditioning performance in shampoo and conditioner applications. In skin care applications, skin lubricity or reduced friction or softer feel of the skin, reduced water vapor transmission, and improved skin elasticity are test methods used to measure skin conditioning. In surfactant-based household cleansing product formulations where conditioning performance is desired such as dish detergents, fabric softeners, and antistatic products, conditioning refers to imparting a softer feel to fabric and eliminating static effects, eliminating fabric fiber breakage or deformation known as pilling. Imparting color retention properties to fabrics is also important and can be measured.

Standard Testing Procedures

Silicone deposition can be measured by several techniques. One technique used for quantifying silicone deposition for Examples of the presently disclosed and/or claimed inventive concept(s) is described as follows.

1. Silicone Deposition Measurement

Each 2-5 gram sample was weighed to the nearest mg, after removal of sample holder, and placed into clean 8-oz jars with approximately 150 ml of methylene chloride. The samples were shaken for 1.5 hours at room temperature. The methylene chloride supernatant was filtered using Whatman #41 filter paper and quantitatively transferred to clean 8-oz jars and evaporated to dryness with mild heat and a nitrogen sparge. Each sample was then dissolved into 2 ml of chloroform-d and quantitatively transferred to a 5-ml volumetric flask. Three chloroform-d rinses were used to transfer each sample to the 5-ml volumetric flask. All flasks were diluted to the mark with solvent and inverted. Each sample was examined in a NICOLET MAGNA 550 FT-IR with 150 co-added scans at 4 $cm^{-1}$ resolution and 0.4747 velocity using a 0.1 cm-fixed path salt cell. A chloroform-d reference spectrum was used to subtract out the solvent bands (diff=1.0). The silicone level was determined by measuring the peak height of the Si—$CH_3$ stretch at 1260 $cm^{-1}$ (baseline 1286 and 1227 $cm^{-1}$) followed by conversion to mg/ml of silicone using a low level calibration curve extending from 10-300 parts per million (ppm). Each sample was corrected for dilution volume and sample weight. All values are reported to the nearest ppm.

2. Formulation I—Surfactant Premix

|  | Grams | % active |  |
| --- | --- | --- | --- |
| ALS[1] | 654 | 11.44643 | STEPANOL ® AM |
| ALES[2] | 213 | 3.727966 | STEOL ® CA-330 |
| CAPB[3] | 175 | 3.062883 | AMPHOSOL ® CA |
| Coco MEA[4] | 16 |  |  |
| DI Water | 543.6 |  |  |
| Wt % Ingredient in shampoo[5] | | | |
| ALS |  | 8.699287 |  |
| ALES |  | 2.833254 |  |
| CAPB |  | 2.327791 |  |
| Total |  | 13.86033 |  |

[1]Ammonium Lauryl Sulfate - STEPANOL ® AM (Stepan Company, Northfield, IL)
[2]Ammonium Laureth Sulfate (3 EO) - STEOL ® CA-330 (Stepan Company, Northfield, IL)
[3]Cocamidopropyl Betaine - AMPHOSOL ® CA (Stepan Company, Northfield, IL)
[4]Coco Monoethanolamide - NINOL ® CMP (Stepan Company, Northfield, IL)
[5]Use 76 grams premix per 100 grams shampoo

3. Procedure for Preparing Silicone Shampoos from Premix Formulation I—Lightly Bleached European Medium Brown Hair Seventy-six grams of Formulation I surfactant premix were weighed into a 4-oz. glass jar. Ten grams of 2 wt % polymer solutions and 9 grams additional water were then weighed into the 4-oz. jar containing the 76 grams Formulation I surfactant premix. The 4-oz jar was then clamped into a 60° C. water bath. A twin-propeller mixer was lowered into the jar and the jar opening was covered with a lid to reduce evaporation loss.

The sample was stirred for 15-minutes. After the 15-minutes of stirring, 0.25 g of $NH_4Cl$ (ammonium chloride Baker reagent) was added to the jar. The sample was then stirred for an additional 45 minutes while covered. The sample jar was then removed from the 60° C. bath. The jar was then clamped into a room temperature water bath. The overhead stirrer was reattached and the stirring of the sample was begun in the water bath. The sample was allowed to stir for a minimum of 5-minutes. This was sufficient time for the sample temperature to drop below 35° C.

3.68 g of dimethiconol, specifically SM™ 555 (Momentive Specialty Chemicals Inc., Columbus, Ohio), was added to the jar and the jar was stirred for a minimum of 5-minutes additionally. 0.5 g of GERMABEN® II (ISP, Wayne, N.J.) product was added to the jar and the jar was stirred for an additional minimum amount of time of 5-minutes.

The pH was checked and adjusted to 6.2-6.5 (either a 10% or 50% solution of citric acid was used to lower the pH). The jar was sealed and centrifuged for about 10-minutes at 3,000 rpm to remove any entrapped air.

The Brookfield viscosity equilibration was measured for 1 hour on a Brookfield LV-4, at 25.0° C., @ 0.3 RPM, then 12 RPM, then 30 RPM. A 3-minute rotation time was used at each speed.

4. Procedure for Preparing Silicone Shampoos from Premix Formulation I—Virgin European Medium Brown Hair The same premix Formulation I was used to prepare shampoos for testing on virgin brown hair, however, the polymer concentration in the shampoo was 0.4 wt %, the amount of ammonium chloride used in these shampoos was 1.0 gram, and the amount of silicone used was 2.45 g of SM™ 555 (ISP, Wayne, N.J.).

5. Wet/Dry Comb Performance Measurement—Lightly Bleached European Medium Brown Hair Conditions Measured at constant temperature and humidity (72 deg. F. and 50% relative humidity). An Instron 1122 (2-lb. load cell, 500-gram range) was used to measure the wet/dry comb performance. Each tress was washed twice with SLS using the standard washing/rinsing procedure. The twice washed tress was hand combed 5-times with large teeth comb and 5-times with small teeth comb (10× total). No Instron testing of SLS-washed tresses. The washed tresses were allowed to sit overnight. No dry-combing. Each tress was shampooed twice with the agreed upon shampoo amount (0.5 g shampoo per 1 gram tress—all tresses were 3.0 g). Each shampooed tress was hand combed twice with a large teeth comb. The hand combed twice tress was loaded into an Instron instrument and the crosshead was lowered to bottom stop. The tress was combed twice with small teeth comb and placed into double-combs. The Instron was run under standard conditions. After the test was run, the tress was sprayed with DI water to keep moist. Using a paper towel, the excess liquid was wiped off double-combs. The crosshead was returned to bottom stop and the tress was replaced into double-combs. The test was rerun under standard conditions. A total of eight tests were run on each tress. After the eight tests were finished, the tress was hung up overnight. The next day, each tress was dry combed tested eight times. No hand combing of dry tresses was done. Averaged wet comb energy for 40 Instron runs and reported average with standard deviation. Averaged dry comb energy for 40 Instron runs and reported average with standard deviation.

A similar combing protocol was used for virgin hair, but only two tresses were used, and the average reported from the two tresses combed 5 times per tress with more pre-combing of the tresses prior to measurement.

Several examples of the above technologies were demonstrated in the following Examples 1-6 in shampoo Formulation I using the standard combing protocol on bleached hair and virgin brown hair. This formulation is shown only for example and other formulations containing other silicones, or other oils, such as mineral oil or any other commonly used conditioning oil, humectants such as glycerol, or conditioning ingredients, such as panthenoic acid or derivatives can be included.

6. Measurement and Calculation of Alkyl Ether Content

The alkyl ether content of the substituted cellulose ethers shown in the examples is determined by reacting a sample with concentrated hydriodic acid at elevated temperature to produce alkyl iodides at temperatures of about 185° C. for 2 hours. The reaction products are extracted in situ into a solvent (o-xylene) and the alkyl iodides are quantified by gas chromatography. This is the so called sealed tube Zeisel—GC technique. The amount of alkyl iodide produced by the sample is converted into the desired equivalent alkyl compound or functional group by multiplying by the ratio of molecular weights:

Species $A \times (mw\ B/mw\ A)$=Species $B$

Specifically for cetyl content:

% cetyl iodide×$mw$ cetyl/$mw$ cetyl iodide=% cetyl

% cetyl iodide×225.45/3552.35=% cetyl

Weight average molecular weights were determined using aqueous size exclusion chromatography.

Example 1

A gel of a water-soluble cetyl-modified hydroxyethyl cellulose (C16 HMHEC, 1.14 wt % cetyl substitution, 3.8 molar hydroxyethyl substitution, Mw=824,000 Dalton) that formed above 1.5-2 wt % polymer concentration and underwent syneresis upon dilution in water was used in this example and showed very good efficacy in a 2-in-1 conditioning shampoo without the need for any cationic moiety and without depositing any silicone. For bleached hair, wet hair comb energy was reduced 30% relative to the wet comb energy for the no polymer control shampoo, and silicone deposition was less than 10 ppm. Wet comb energies for the shampoo containing the cationic guar benchmark, N-HANCE® 3916 product, were reduced 40% relative to the no polymer shampoo.

This example demonstrates that the nonionic hydrophobic polymer that undergoes syneresis in aqueous solution or in the shampoo on dilution can achieve nearly 75% of the wet comb energy reduction achieved by the cationic polymer. The dry comb energies for the tresses treated with a shampoo containing the polymers of the invention were equal to the dry comb energy measured on tresses treated with the shampoo containing no polymer and the shampoo containing cationic guar.

Example 2

A water-soluble C16 HMHEC (1.04 wt % cetyl substitution, 4.0 molar hydroxyethyl substitution, Mw=1,200,000 Dalton) was used in this Example. This polymer formed a gel at 3-4 wt % polymer in water but showed syneresis at 2 wt %, was dissolved in 5 wt % ammonium lauryl sulfate to give a clear solution, and underwent syneresis upon dilution with water. This polymer showed very good efficacy in 2-in-1 conditioning shampoos without the need for any cationic moiety and without depositing any silicone. For bleached hair, wet hair comb energy was reduced by 28% relative to the no polymer control shampoo, and silicone deposition was less than 10 ppm. Wet hair comb energy reduction was 70% of the wet comb energy reduction achieved by cationic guar. The dry comb energies for the tresses treated with a shampoo containing the polymers of the invention were equal to the dry comb energy measured on tresses treated with the shampoo containing no polymer and the shampoo containing cationic guar.

(Example 3) Comparative

A shampoo was made with a water-soluble cetyl-modified hydroxyethyl cellulose (POLYSURF® 67 product, 0.5 wt % cetyl substitution, 2.5 molar hydroxyethyl substitution, Mw=830,000 Dalton) that did not form a gel above 1.5-2 wt % polymer concentration and did not undergo syneresis upon dilution in water. For bleached hair, wet hair comb energy was reduced by 13% relative to the wet comb energy for the no polymer control shampoo, and silicone deposition was less than 10 ppm.

This example demonstrates that the nonionic hydrophobic polymer that does not undergo syneresis does not show as good efficacy in the 2-in-1 conditioning shampoo as a polymer that undergoes dilution deposition (Examples 1-3). The dry comb energies for tresses treated with a shampoo containing the commercial Polysurf 67 product was equivalent, within standard deviation, of the dry comb energy measured on tresses treated with the shampoo containing no polymer and the shampoo containing cationic guar.

(Example 4) Comparative

An HMHEC polymer that was water-insoluble (2.82 wt % cetyl substitution, 3.83 molar hydroxyethyl substitution), dissolved with added surfactant in shampoo, yet did not undergo syneresis upon dilution and hence showed low efficacy in wet comb reduction. For bleached hair, wet hair comb energy was reduced by 11% relative to the wet comb energy for the no polymer control shampoo, and silicone deposition was less than 10 ppm. The dry comb energies for the tresses treated with a shampoo containing this polymer were equal to the dry comb energy measured on tresses treated with the shampoo containing no polymer and the shampoo containing cationic guar. This example demonstrates that water-insolubility is not a defining criteria for performance, and syneresis of the water-insoluble polymer is required for performance.

Example 5

A gel of a water-soluble methylphenylglycidyl hydroxyethyl cellulose ether, (6.3 wt % methylphenyl substitution, 2.5 molar hydroxyethyl substitution, Mw=350,000 Dalton), formed a gel above 1.5-2 wt % polymer concentration and underwent syneresis upon dilution in water and showed good efficacy in 2-in-1 conditioning shampoos without the need for any cationic moiety and depositing less than 30 ppm silicone. For virgin medium brown European hair, wet hair comb energy reduction was 72% of the wet comb energy reduction achieved by cationic guar. A silky feel was imparted to the hair.

Wet comb energy for the shampoo containing the cationic guar benchmark, N-HANCE® 3916 product, was reduced 61% relative to the no polymer shampoo, with greater than 40 ppm silicone deposited. This example demonstrated that the nonionic hydrophobic polymer that undergoes syneresis in aqueous solution or in the shampoo on dilution can achieve nearly 74% of the wet comb energy reduction achieved by the cationic polymer on virgin hair, with less silicone deposition. The dry comb energies for the tresses treated with a shampoo containing the polymer of the invention were equal to the dry comb energy measured on tresses treated with the shampoo containing no polymer and the shampoo containing cationic guar.

Examples 6-28

Simple conditioning tests were performed evaluating polymers of the invention and some commercial polymers on mildly bleached hair using a fully formulated rinse-off conditioner (Examples 6-16) and aqueous solutions of the polymers (Examples 17-28). The Instron comb test described below was used to generate the data shown in these Examples. Comparison of the wet and dry comb energy Example 16 with other Examples in the Table demonstrated that the polymer of the invention delivered the lowest combined wet and dry comb energies of all nonionic and hydrophobic polymers tested and approached the wet and dry comb energies delivered by cationic polymers of Example 8. In Table 2, comparison of the wet and dry comb energy Example 28 with other examples in the Table 2 demonstrated that the polymer of the invention delivered the lowest combined wet and dry comb energies of all nonionic and hydrophobic polymers tested and approached the wet and dry comb energies delivered by cationic polymers of Examples 18-20.

Table 1—Polymers as a Conditioner in Fully Formulated Conditioning Formulation 1

NATROSOL® (Hercules, Inc., Wilmington, Del.) hydroxyethyl cellulose type 250HHR was added to water under agitation. Next, pH was adjusted to 8.0 to 8.5. The slurry was stirred for about 30 minutes or until polymer dissolved. Next, polymer of this invention or a commercial comparative polymer listed in TABLE 1 was added and mixed for 30 more minutes. The solution was heated to about 65° C. and stirred until it became smooth. Cetyl alcohol was added and mixed until it mixed homogeneously. The mixture was cooled to about 50° C. and then potassium chloride was added. Next, isopropyl myristate was added and mixed until the mixture looked homogeneous. The pH of the mixture was adjusted between 5.25 to 5.5 with citric acid and/or NaOH solution. The conditioner was preserved with 0.5% preservative and mixed until it reached room temperature.

| | |
|---|---|
| 90.94 g | Deionized water |
| 00.70 g | NATROSOL ® 250HHR |
| 00.20 g | Polymer of this invention or commercial polymer |
| 02.00 g | Cetyl alcohol |
| 00.50 g | Potassium Chloride |
| 02.00 g | Isopropyl Palmitate |
| As required | Citric acid to adjust pH |
| As required | Sodium hydroxide to adjust pH |
| 00.50 g | Preservative |

About three grams in weight flat tresses of mildly bleached European hair from International Hair Importers and Products Inc. of Glendale, N.Y. were used for measuring wet and dry combing performance of various formulations of this experiment. To clean the hair tress, the hair tress was first wet with 40° C. tap water and then 5.0 ml of sodium lauryl sulfate solution was applied along the tress length. Tress was kneaded for 30 second. Tress was then rinsed under 40° C. running water for 30 seconds followed by rinsing with room temperature tap water for 30 seconds. The tress was then dried overnight. Next day, the tress was rewet with 40° C. tap water. Next, 0.5 grams of test conditioner per gram of hair was applied uniformly along the length of hair. Tress was kneaded for 30 seconds and then it was rinsed under 40° C. running water for 30 seconds. The conditioner was reapplied along the length of the tress and the tress was kneaded for 30 seconds; then, it was rinsed under 40° C. running water for 30 seconds. The tress was rinsed with room temperature tap water for 30 seconds. The tress was combed immediately eight times and from the data average amount combing energy in gram force-mm/gram of hair (gf-mm/g) required to comb the hair was calculated. The tress was stored overnight at about 50% relative humidity and about 23° C. Next day, the tress was first combed with fine teeth rubber comb to free-up hair stuck together. Again, the hair tress was combed eight times to determine the average force required to comb one gram of dry hair. The higher the number the poorer the conditioning effect of the polymer being tested. Two tresses were used per conditioning formulation. The data reported below are average of two tresses.

TABLE 1

| Example# | Polymer | Comparative Polymer | Polymer type | Polymer Level/wt % | Conditioner Viscosity (cps) | Wet Combing (gf-mm/g) | Dry Combing (gf-mm/g) | Comments |
|---|---|---|---|---|---|---|---|---|
| 6 | | Polymer-Free Control | — | 0 | 990 | 4774 | 287 | Stable |
| 7 | | Polymer-Free Control | — | 0 | 1380 | 4513 | 364 | Stable |
| 8 | | NHANCE ® 3269 | cationic | 0.2 | 1330 | 1389 | 263 | Stable |
| 9 | | NATROSOL ® 250HHR | nonionic | 0.2 | 1970 | 4320 | 361 | Stable |
| 10 | | NATROSOL ® 250HHR | nonionic | 0.2 | 2100 | 2700 | 290 | Stable |
| 11 | | UCARE ™ LR400 | cationic | 0.2 | 1280 | 811 | 1116 | Stable |
| 12 | | NEXTON ® 3082R | hydrophobic | 0.2 | 2280 | 4941 | 312 | Stable |
| 13 | | NATROSOL ® Plus 330 | hydrophobic | 0.2 | 1670 | 2565 | 340 | Stable |
| 14 | | POLYSURF ® 67 | hydrophobic | 0.2 | 2170 | 2952 | 459 | Stable |
| 15 | | AQU D3673 | hydrophobic | 0.2 | 1080 | 2281 | 625 | Stable |
| 16 | AQU D3930 | | hydrophobic | 0.2 | 1940 | 2262 | 298 | Stable |

Ingredient List for Table 1:
(1) NATROSOI® 250HHR: Hydroxyethyl cellulose from Hercules, Inc., Wilmington, Del.
(2) NEXTON® 3082R: C4 hydrophobically modified hydroxyethyl cellulose from Hercules, Inc., Wilmington, Del.
(3) POLYSURF® 67: NT4C3594, C16 hydrophobically modified hydroxyethyl cellulose from Hercules, Inc.
(4) NATROSOL® Plus 330: NT43669, C16 hydrophobically modified hydroxyethyl cellulose from Hercules, Inc.
(5) UCARE™ LR400: Cationic HEC from Dow Chemicals, Midland, Mich.

(6) UCARE™ JR30M: Cationic HEC from Dow Chemicals, Midland, Mich.
(7) N-HANCE® 3269: cationic guar cationic DS 0.13, Weight average Molecular weight 500,000 from Hercules, Inc., Wilmington, Del.
(8) AQUACAT® CG 518: cationic guar, cationic DS 0.18, Weight average Molecular weight 50,000 from Hercules, Inc., Wilmington, Del.
(9) AQU D3930: Polymer of this invention, C16 hydrophobically modified hydroxyethyl cellulose from Hercules, Incorporated 0.62 wt % cetyl, hydroxyethyl molar substitution (HEMS) 4.0
(10) AQU D3673: C8 hydrophobically modified hydroxyethyl cellulose from Hercules, Inc.
(11) CRODACOL® C95NF: Cetyl alcohol from Croda Inc. Parsippany, N.J.
(12) KCl: Potassium chloride
(13) STEPAN® IPM: Isopropyl myristate from Stepan Company, Northfield, Ill.
(14) GERMABEN® II: preservative from ISP, Wayne, N.J.

Table 2—Polymers as a Detangling Agent/Conditioning Agent in Aqueous System

Polymers of this invention or comparative polymers, listed in Table 2, were added to water under agitation to form a slurry. Next, pH was adjusted to between 8.0 to 8.5 for cellulosic polymers and to about 6.5 for guar based products. The slurry was mixed for about 60 minutes or until the polymer fully dissolved. Then, the pH of the mixture was adjusted to between 5.25 to 5.5 with citric acid and/or NaOH solution. The conditioner was preserved with 0.1% preservative and mixed for 15 minutes. The pH was readjusted as necessary.
Ingredients:

| | |
|---|---|
| 99.70 g | Deionized water |
| 00.20 g | Polymer of this invention or commercial polymer |
| As required | Citric acid to adjust pH |
| As required | Sodium hydroxide to adjust pH |
| 00.10 g | Preservative |

About three grams in weight of flat tresses of mildly bleached European hair from International Hair Importers and Products Inc. of Glendale, N.Y. were used for measuring wet and dry combing performance of various formulations of this example. To clean the hair tress, the hair tress was first wet with 40° C. tap water and then 5.0 ml of sodium lauryl sulfate solution was applied along the tress length. The tress was kneaded for 30 second. The tress was then rinsed under 40° C. running water for 30 seconds followed by rinsing with room temperature tap water for 30 seconds. The tress was then dried overnight. Next day, the tress was rewet with 40° C. tap water. Next, 0.5 grams of test solution per gram of hair was applied uniformly along the length of hair. The tress was kneaded for 30 seconds and then was rinsed under 40° C. running water for 30 seconds. The test solution was reapplied along the length of the tress and the tress was kneaded for 30 seconds and then was rinsed under 40° C. running water for 30 seconds. The tress was rinsed with room temperature tap water for 30 seconds. The tress was combed immediately eight times to calculate the average amount of combing energy in gram force-mm/gram of hair (gf-mm/g) required to comb the hair. The tress was stored overnight at about 50% relative humidity and about 23° C. Next day, the tress was first combed with fine teeth rubber comb to free-up hair stuck together. Again, hair tress was combed eight times to determine average force required to comb one gram of dry hair. The higher the number, the poorer the conditioning effect of the polymer being tested. Two tresses were used per conditioning formulation. Combing data below are average of two tresses.

TABLE 2

| Example # | Polymer | Polymer Type | Comparative Polymer | Lot# | Wet Combing (gf-mm/g) | Dry Combing (gf-mm/g) |
|---|---|---|---|---|---|---|
| 17 | | — | Polymer-free Control | | 5267 | 318 |
| 18 | | Cationic | N-HANCE ® 3269 | | 1553 | 497 |
| 19 | | Cationic | AQUACAT ® CG518 | | 1123 | 185 |
| 20 | | Cationic | N-HANCE ® 3196 | | 1830 | 659 |
| 21 | | Nonionic | NATROSOL ® 250HHR | | 2811 | 314 |
| 22 | | Cationic | UCARE ™ LR400 | | 607 | 515 |
| 23 | | Cationic | UCARE ™ JR30M | | 759 | 334 |
| 24 | | Hydrophobic | NEXTON ® 3082R | | 5631 | 410 |
| 25 | | Hydrophobic | NEXTON J20R | | 5774 | 434 |
| 26 | | Hydrophobic | NATROSOL ® Plus 330 | | 2059 | 333 |
| 27 | | Hydrophobic | POLYSURF ® 67 | | 2451 | 451 |
| 28 | AQU D3930 | Hydrophobic | | | 1798 | 463 |

Ingredient List for Table 2:
(1) NATROSOL® 250HHR: Hydroxyethyl cellulose from Hercules, Inc., Wilmington, Del.
(2) NEXTON® 3082R: C4 hydrophobically modified hydroxyethyl cellulose from Hercules, Inc., Wilmington, Del.
(3) NEXTON® J20R, C4 hydrophobically modified hydroxyethyl cellulose from Hercules, Inc., Wilmington, Del.
(4) POLYSURF® 67: NT4C3594, C16 hydrophobically modified hydroxyethyl cellulose from Hercules, Inc.
(5) NATROSOL® Plus 330: NT43669, C16 hydrophobically modified hydroxyethyl cellulose from Hercules, Inc.
(6) UCARE™ LR400: Cationic HEC from Dow Chemicals, Midland, Mich.
(7) UCARE™ JR30M: Cationic HEC from Dow Chemicals, Midland, Mich.
(8) N-HANCE® 3269: cationic guar cationic DS 0.13, Weight average Molecular weight 500,000 from Hercules, Inc., Wilmington, Del.

(9) N-HANCE® 3196: cationic guar cationic DS 0.13, Weight average Molecular weight 1.2 MM from Hercules, Inc., Wilmington, Del.
(10) AQUACAT® CG 518: cationic guar, cationic DS 0.18, Weight average Molecular weight 50,000 from Hercules, Inc., Wilmington, Del.
(11) AQU D3930: Polymer of this invention, C16 hydrophobically modified hydroxyethyl cellulose from Hercules, Inc. 0.62 wt % cetyl, hydroxyethyl molar substitution (HEMS) 4.0
(12) KATHON™ CG: Preservative from Rohm & Haas Examples 29-39

A skin lotion was prepared containing the polymer of the presently disclosed and/or claimed inventive concept(s) (Example 33) and compared with a polymer-free skin lotion (Example 30), skin lotions containing hydrophobic polymers which did not undergo syneresis (Examples 32, 36, 40) and with skin lotions containing commercial nonionic and cationic polymers. The skin lotion containing the polymer of the invention showed increased viscosity and structure as compared with the polymer-free control formulation in Example 30. Example 33 was more stable than the formulations containing cationic polymer. Compared with the commercial hydrophobic polymers, the polymer of the invention appeared slightly grainy, suggesting that this polymer could be used at a lower concentration than commercial hydrophobic polymers.

TABLE 3

Fully Formulated Skin Lotion - Single Polymer

| Ingredient | Weight % Active |
| --- | --- |
| A. Polymer | 0.50 |
| Distilled water | 78.00 |
| Glycerin | 2.00 |
| B. Glycol stearate (KESSCO ® EGMS) | 2.75 |
| Stearic acid (INDUSTRENE ® 5016) | 2.50 |
| Mineral oil (DRAKEOL ® 7) | 2.00 |
| Acetylated lanolin (LIPOLAN ® 98) | 0.50 |
| Cetyl alcohol (CRODACOL ® C95) | 0.25 |
| C. Distilled water | 10.00 |
| Triethanolamine | 0.50 |
| D. Propylene glycol and diazolidinyl urea and methylparaben and propylparaben (GERMABEN ® II) | 0.75 |
| Total: | 100.00 |

Procedure:

The polymer listed in Table 3 was dispersed in water by adding to the vortex of well-agitated from Part A. It was mixed for five minutes. Next, glycerin was added with continued mixing and heated to 80° C. Mixed 15 minutes at 80° C. In a separate vessel, blended Part B ingredients and heated to 80° C. and mixed well.

Part A was added to Part B with good agitation while maintaining an emulsion temperature at 80° C. Part C ingredients were mixed together in a vessel and added to the emulsion of Parts A and B. The new mixture was mixed continuously while cooling to 40° C. Then, the pH was adjusted between 6.0 to 6.5. Then Part D, a preservative, was added to the emulsion and mixed well. The new emulsion was then cooled and filled.

TABLE 4

| Example# | Polymer | Polymer Type | Commercial Polymer | Lotion Viscosity at 5 rpm | pH | Comments |
| --- | --- | --- | --- | --- | --- | --- |
| 30 |  | — | Control - Polymer-Free | 6,800 | 6.3 | Fluid |
| 31 |  | hydrophobic | NATROSOL ® Plus 330 | 124,000 | 6.2 | Smooth, glossy, cream |
| 32 |  | cationic | N-HANCE ® 3215 |  |  | Phase separation |
| 33 | AQU D3930 | hydrophobic |  | 164,000 | 6.4 | Stable, grainy, Highly structured |
| 34 |  | cationic | UCARE ™ LR400 | 28,000 | 6.2 | Curdled appearance. No separation |
| 35 |  | cationic | UCARE ™ JR30M | 19,200 | 6.1 | Curdled appearance. No separation |
| 36 |  | hydrophobic | POLYSURF ® 67 | 165,000 | 6.4 | Stable, glossy, Highly structured |
| 37 |  | nonionic | NATROSOL ® 250M | 5,600 | 6.3 | Fluid, Glossy |
| 38 |  | nonionic | NATROSOL ® 250LR | 4,400 | 6.6 | Fluid, Glossy |
| 39 |  | hydrophobic | AQU D3673A | 10,800 | 6.5 | Fluid, Glossy |
| 40 |  | hydrophobic | NEXTON ® 3082R |  |  |  |

Ingredient List for Table 4:
(1) KESSCO® EGMS: Stepan Company, Northfield, Ill.
(2) INUSTRENE® 5016: Crompton Corp., Middlebury, Conn.
(3) DRAKEOL® 7: Penreco, Pennzoil Products Company, Karn City, Pa.
(4) LIPOLAN® 98: Lipo Chemicals., Inc., Paterson, N.J.
(5) CRODACOL® C95: Croda Inc., Parsippany, N.J.
(6) GERMABEN® II: preservative from ISP, Wayne, N.J.
(7) NATROSOL® Plus 330: C16 Hydrophobically modified Hydroxyethyl cellulose Hercules, Inc., Wilmington, Del.
(8) N-HANCE® 3215: Cationic guar, Hercules, Inc., Wilmington, Del.
(9) AQU D3930: Polymer of this invention, C16 hydrophobically modified hydroxyethyl cellulose from Hercules, Inc., 0.62 wt % cetyl, hydroxyethyl molar substitution (HEMS) 4.0
(10) UCARE™ LR400: Cationic HEC from Dow Chemicals, Midland, Mich.
(11) UCARE™ JR30M: Cationic HEC from Dow Chemicals, Midland, Mich.
(12) POLYSURF® 67: NT4C3594, hydrophobically modified hydroxyethyl cellulose from Hercules, Inc.
(13) NATROSOL® 250LR: lot#28667, Hydroxyethyl cellulose from Hercules, Inc., Wilmington, Del.
(14) NATROSOL® 250M: Hydroxyethyl cellulose from Hercules, Inc., Wilmington, Del.
(15) NEXTON® 3082RC4: Hydrophobically modified hydroxyethyl cellulose from Hercules, Inc., Wilmington, Del.
(16) NATROSOL® 250HHR CS: Hydroxyethyl cellulose from Hercules, Inc., Wilmington, Del.
(17) AQU D3673: C8 hydrophobically modified hydroxyethyl cellulose from Hercules, Inc.

Examples 41-51

A body wash formulation was prepared using the polymer of the presently disclosed and/or claimed inventive concept(s) (Example 43) with a polymer-free control (Example 41) and with formulations containing commercial nonionic, hydrophobic, and cationic polymers. The polymer of the presently disclosed and/or claimed inventive concept(s) (Example 43) showed better compatibility with the body wash components than the nonionic commercial polymers (Examples 48 and 50). The commercial hydrophobic polymers conveyed an applesauce texture to the formulation as did the polymer of the presently disclosed and/or claimed inventive concept(s). This result suggests that these polymers could be used at a lower concentration in this formulation.

Body Wash Table 5

Body wash preparation: An aqueous stock solution of each polymer was first prepared at 1.0% concentration. For polymers: N-HANCE® 3215, ADPP6503, AQU D3799, and AQU D3939 solutions were made by adding polymer to water under vigorous agitation. Next, the pH was lowered to between 6 to 7 with citric acid and the solution was mixed for an hour or until the polymer solubilized. The solutions were preserved with 0.5% Glydant® product. For the polymers ADPP6531, ADPP5922, AQU D3869, AQU D3673, ADPP6582 ADPP6626, POLYSURF® 67, NATROSOL® plus 330, NATROSOL® 250HHR, NATROSOL® 250M, UCARE™ JR30M, UCARE™ JR400, AQU D3686 ADPP6641, the polymers were added to well agitated water and then the pH was raised to 8.5 to 9.5 using sodium hydroxide. The solution was mixed for an hour and then the pH was lowered to between 6 to 7 using citric acid.

Body wash stock solution was prepared by adding to vessel 46.4 grams of sodium laureth sulfate, 27.0 grams of sodium lauryl sulfate, 6.7 grams of $C_9$-$C_{15}$ alkyl phosphate, 4.0 grams of PPG-2 hydroxyethyl cocamide, 1.0 gram of sodium chloride, 0.30 gram of tetra sodium EDTA, and 0.5 gram of DMDM hydantoin in the order listed while mixing. Each ingredient was allowed to mix homogeneously before adding the next ingredient. The total stock solution weighed 85.9 grams.

Body wash was prepared by adding 20 grams of polymer (listed in Table 4) solution to 80 grams of the above body wash stock solution while mixing. Next, the body wash pH was adjusted to between 6 and 7 with citric acid. The body wash viscosity was measured using the Brookfield LVT viscometer. The viscosity was measured at 30 rpm once the body wash conditioned for at least two hours at 25° C. The body wash clarity was also measured at 600 nm using a Spectrophotometer, Cary 5E UV-VIS-NIR, available from Varian Instruments, Inc. The clarity measurements at 600 nm wavelength are reported as % T value. The higher the number, the clearer is the solution.

Lather Drainage Test:

Objective of this test is to measure the lather drainage time of a diluted body wash solution. Long drainage times indicate a rich, dense lather with good stability. The test was used to determine the influence that the polymers of this invention may have on lather quality. The relevant equipment: a WARING® Blender Model #7012 or 34BL97 or equivalent; a funnel, preferably plastic; 6" diameter, 7/8" ID neck, 5¼" high, with a horizontal wire 2" from the top; a U.S.A. Standard Testing Sieve NO. 20 or TYLER® Equivalent 20 mesh or 850 micrometer or 0.0331 inch sieve (preferably over 7 inch in diameter but smaller size could also be used); and a stopwatch or a timer. For each test formulation, 1,000 g of a diluted body wash solution was prepared as shown below.

| | |
|---|---|
| Body wash | 66.13 g |
| Deionized Water | 933.87 g |
| Total | 1,000.00 g |

For each lather test measurement, 200 grams of above diluted solution was weighed and placed in a 25° C. waterbath for 2 hours. Three jars (each with 200 grams of solution) were prepared per body wash formulation. Next, the lather drainage time for each solution was measured using the following procedure: 200 g of solution was poured into a clean, dry Waring® blender glass vessel; the solution was blended at the highest speed for exactly 1 minute while covered; the foam generated in the jar was immediately poured into a clean, dry funnel standing on a 20 mesh screen over a beaker and the foam from the blender was poured for exactly 15 seconds (the goal was to get as much foam as possible into the funnel without overflowing); after 15 seconds, stopped pouring foam, however, the stopwatch was kept running; and, the total time needed for the foam to drain including the 15 seconds for pour time was recorded once the wire was no longer covered by foam or liquid.

TABLE 5

| Example # | Polymer | Polymer Type | Commercial Polymer | Visc. Cps | Lather Stability Seconds | T (%) | Comments |
|---|---|---|---|---|---|---|---|
| 41 | — | | Control - Polymer-Free | 3680 | 54 | 99.4 | |
| 42 | | Cationic | N-HANCE ® 3215 | 6100 | 98.7 | 85.9 | |
| 43 | AQU D3930 | Hydrophobic | | 3960 | 57.3 | 25.2 | Applesauce like structure, separation |
| 44 | | Cationic | UCARE ™ JR400 | 6420 | 52.7 | 78.8 | |
| 45 | | Cationic | UCARE ™ JR30M | 19120 | 57.5 | 98.5 | |
| 46 | | Hydrophobic | NATROSOL ® Plus 330 | 4080 | 64.3 | 21.6 | Applesauce like structure |
| 47 | | Hydrophobic | POLYSURF 67 | 4080 | 52.3 | 14.2 | Applesauce like structure |
| 48 | | Nonionic | NATROSOL ® 250M | 4540 | Not Run | 32.4 | Gels-Incompatible |
| 49 | | Hydrophobic | NEXTON ® 3082R | 4420 | 53.3 | | |
| 50 | | Nonionic | NATROSOL ® 250HHR CS | 4680 | Not run | 52.1 | Gels-Incompatible |
| 51 | | Hydrophobic | AQU D3673A | 3560 | 60 | 95.5 | |

Ingredient List for Table 5:
(1) Sodium Lauryl Sulfate—STEPANOL® WAC, Stepan Company, Northfield, Ill. 60093.
(2) Sodium Laureth Sulfate—RHODAPEX® ES-2, Rhodia, Cranbury, N.J. 08512
(3) Cocamidopropyl Betaine—AMPHOSOL® CA, Stepan Company, Northfield, Ill. 60093.
(4) PPG-2 Hydroxyethyl Cocamide—PROMIDIUM® CO, Uniqema, Newcastle, Del.
(5) Tetra Sodium EDTA—Fisher Scientific.
(7) DMDM Hydantoin, GLYDANT®, Lonza Inc., Fair Lawn, N.J., USA
(8) Sodium Chloride from Baker.
(9) NATROSOL® Plus 330—NT3J3314, C16 Hydrophobically modified Hydroxyethyl cellulose Hercules Inc., Wilmington, Del.
(10) N-HANCE 3215: J4013A, Cationic guar, Hercules, Inc., Wilmington, Del.
(11) AQU D3930: Polymer of this invention, C16 hydrophobically modified hydroxyethyl cellulose from Hercules, Inc., 0.62 wt % cetyl, hydroxyethyl molar substitution (HEMS) 4.0
(12) UCARE™ JR400: Cationic HEC from Dow Chemicals, Midland, Mich.
(13) UCARE™ JR30M: Cationic HEC from Dow Chemicals, Midland, Mich.
(14) POLYSURF® 67: NT4C3594, hydrophobically modified hydroxyethyl cellulose from Hercules, Inc.
(15) NATROSOL® 250M: Hydroxyethyl cellulose from Hercules, Inc., Wilmington, Del.
(16) NEXTON® 3082R: Hydrophobically modified hydroxyethyl cellulose from Hercules, Inc., Wilmington, Del.
(17) NATROSOL® 250HHR CS, Hydroxyethyl cellulose from Hercules, Inc., Wilmington, Del.
(18) AQU D3673: C8 Hydrophobically modified hydroxyethyl cellulose from Hercules, Inc.

Examples 52-62

The polymer of the presently disclosed and/or claimed inventive concept(s) was incorporated into a sunscreen formulation (Example 54). The formulation was stable.

Sunscreen Lotion—Table 6

The Drakeol mineral oil was heated in a vessel to 75° C. while mixing. Next, the remaining ingredients of Part A (Arlmol E, Neo Heliopan AV, Uvinol M40, Castor wax, Crill-6, Arlatone T, Ozokerite wax and Dehymuls HRE7) were added to the vessel in the order listed while mixing. The mixture was mixed for 30 minutes at 70° C. In a separate container water of Part B was heated to 70° C. Next, the polymer of invention or comparative polymer (listed in Table 5) was added and mixed until dissolved and then Glycerine was added and mixed. In a separate container, a solution of magnesium sulfate was prepared by adding magnesium sulfate to water. Next, the solution of magnesium sulfate was added to Part B and mixed until heated back to 70° C. This mixture was then added to Part A while mixing and then mixed for 30 minutes at 70° C. and then cooled to room temperature while mixing. Preservative Germaben II was added when temperature reached below 50° C.

TABLE 6

| Ingredient | Amount |
|---|---|
| Part A: | |
| DRAKEOL ® 7: Mineral oil | 13.0 g |
| ARLAMOL ™ E: PPG-15 Stearyl ether | 6.0 g |
| NEO HELIOPAN ® AV: Octyl methoxcinnamate | 1.0 g |
| UVINOL ® M40: Benzophenone-3 | 1.0 g |
| Castor Wax: Hydrogenated castor oil | 1.4 g |
| CRILL ™ 6: Sorbitan iostearate | 1.2 g |
| ARLATONE ® T: PPG-40 Sorbitan Peroleate | 1.0 g |
| Ozokerite Wax 77W: Wax | 1.0 g |
| DEHYMULS ® HRE7: PEG-7 hydrogenated castor oil | 0.5 g |
| Part B: | |
| Deionized water | 40.5 g |
| Polymer | 0.5 g |
| Glycerine | 3.0 g |
| Part C: | |
| Deionized water | 23.1 g |
| Magnesium Sulfate | 0.7 g |
| Part D: | |
| Germaben ® II - Preservative | 0.5 g |

| Example # | Polymer | Polymer Type | Commercial Polymer | Visc. cps | Comments |
|---|---|---|---|---|---|
| 52 | | | Control - Polymer-Free | 4400 | |
| 53 | | | N-HANCE ® 3215 | 2440 | |

TABLE 6-continued

| 54 | AQU D3930 | | 6060 |
| 55 | | UCARE ™ JR400 | 8120 |
| 56 | | UCARE ™ JR30M | 3516 |
| 57 | | NATROSOL ® Plus 330 | 5880 |
| 58 | | POLYSURF ® 67 | 5260 |
| 59 | | NATROSOL ® 250M | 3540 |
| 60 | | NEXTON ® 3082R | 5700 |
| 61 | | NATROSOL ® 250HHR CS | 2500 |
| 62 | | AQU D3673A | Phase separation |

Ingredient List for Table 6:
(1) DRAKEOL® 7: Mineral oil, Penereco, Karn City, Pa.
(2) ARLAMOL™ E: OOG-15 Stearyl ether, Uniqema Americas, New Castle, Del.
(3) NEO HELIOPAN® AV: Octyl methoxcinnamate, Symrise, Totowa, N.J.
(4) UVINOL® M40: Benzophenone-3, BASF, Mount Olive, N.J.
(5) Castor Wax: Hydrogenated castor oil, Frank B. Ross
(7) CRILL™ 6: Sorbitan iostearate, Croda, Inc., Parsippany, N.J.
(8) ARLATONE® T: PPG-40 Sorbitan Peroleate, Uniqema Americas, New Castle, Del.
(9) Ozokerite Wax 77W: Wax, Frank B. Ross
(10) DEHYMULS® HRE7: PEG-7 hydrogenated castor oil, Cognis, Amber, Pa.
(11) Magnesium sulfate—J. T. Baker, Phillpsburg, N.J.
(12) Glycerine: Spectrum Bulk Chemicals, New Brunswick, N.J.
(13) Germaben® II—Preservative, Cognis, Amber, Pa.
(14) NATROSOL® Plus 330—NT3J3314, C16 Hydrophobically modified Hydroxyethyl cellulose Hercules, Inc., Wilmington, Del.
(15) N-HANCE® 3215—J4013A, Cationic guar, Hercules, Inc., Wilmington, Del.
(16) AQU D3930: Polymer of this invention, C16 hydrophobically modified hydroxyethyl cellulose from Hercules, Inc., 0.62 wt % cetyl, hydroxyethyl molar substitution (HEMS) 4.0
(17) UCARE™ JR400: Cationic HEC from Dow Chemicals, Midland, Mich.
(18) UCARE™ JR30M: Cationic HEC from Dow Chemicals, Midland, Mich.
(19) POLYSURF® 67: NT4C3594, hydrophobically modified hydroxyethyl cellulose from Hercules, Inc.
(20) NATROSOL® 250M: Hydroxyethyl cellulose from Hercules, Inc., Wilmington, Del.
(21) NEXTON® 3082R: Hydrophobically modified hydroxyethyl cellulose from Hercules, Inc., Wilmington, Del.
(22) NATROSOL® 250HHR CS, Hydroxyethyl cellulose from Hercules, Inc., Wilmington, Del.
(23) AQU D3673: 11750-46, C8 Hydrophobically modified hydroxyethyl cellulose from Hercules, Inc.

Examples 63-73

The polymer of the presently disclosed and/or claimed inventive concept(s) was incorporated into a roll-on antiperspirant formulation which was stable (Example 65).

Roll-On Antiperspirant

Table 7
Antiperspirant preparation: An aqueous stock solution of each polymer was first prepared at 1.0% concentration. For polymers (N-HANCE® 3215, ADPP6503, AQU D3799, and AQU D3939), solutions were made by adding the polymer to water under vigorous agitation. Next, the pH was lowered to between 6 to 7 with citric acid and the solution was mixed for an hour or until polymer solubilized. The solutions were preserved with 0.5% Glydant® product. For the polymers ADPP6531, ADPP5922, AQU D3869, AQU D3673, ADPP6582 ADPP6626, POLYSURF® 67, NATROSOL® plus 330, NATROSOL® 250HHR, NATROSOL® 250M, UCARE™ JR30M, UCARE™ JR400, AQU D3686 ADPP6641, the polymer was added to intensely agitated water and then the pH was raised to between 8.5 to 9.5 using sodium hydroxide. The solution was mixed for an hour and then the pH was lowered to between 6 to 7 using citric acid.

A 150 gram batch of roll-on antiperspirant was made using the procedure: 15.0 g of a polymer from the list in Table 6 was added to stock solution in an 8-oz. glass jar and mixed with a magnetic plate and stirrer; next, 22.5 g of deionized water was added to the glass jar and mixing continued for about 30 minutes. While mixing, 45.0 g of ethanol was added and the mixing continued for an additional 10 minutes; and then, 67.5 g of the antiperspirant active Summit ACH303 was added and the mixing continued for 30 more minutes.

TABLE 7

| Example # | Polymer of Invention | Commercial Polymer | Visc. cps | Comments |
|---|---|---|---|---|
| 63 | | Control - Polymer-Free | | Clear, water-white |
| 64 | | N-HANCE ® 3215 | | Very hazy, gels through-out |
| 65 | AQU D3930 | | | |
| 66 | | UCARE ™ JR400 | | |
| 67 | | UCARE ™ JR30M | | |
| 68 | | NATROSOL ® Plus 330 | | Clear, water-white, fine particles throughout |
| 69 | | POLYSURF ® 67 | | Clear, trace haze, fine particles throughout |
| 70 | | NATROSOL ® 250M | | Clear, water-white, fine particles throughout |
| 71 | | NEXTON ® 3082R | | |
| 72 | | NATROSOL ® 250HHR CS | | Clear, water-white, fine particles throughout |
| 73 | | AQU D3673A | | |

Ingredient List for Table 7:
(1) Ethanol: Dehydrated ethanol; Spectrum Chemicals MFG Corp, Gardena, Calif.
(2) SUMMIT ACH-303—50% aqueous solution of Aluminum Chlorohydrate, Summit Research Labs, 45 River Road, Flemington, N.J.
(3) NATROSOL® Plus 330—NT3J3314, C16 Hydrophobically modified Hydroxyethyl cellulose Hercules, Inc., Wilmington, Del.
(4) N-HANCE® 3215: J4013A, Cationic guar, Hercules, Inc., Wilmington, Del.
(5) AQU D3673: 11750-46; Polymer of this invention, C8 Hydrophobically modified hydroxyethyl cellulose from Hercules, Inc.

(6) AQU D3930: Polymer of this invention, C16 Hydrophobically modified hydroxyethyl cellulose from Hercules, Inc., 0.62 wt % cetyl, hydroxyethyl molar substitution (HEMS) 4.0
(7) UCARE™ JR400: Cationic HEC from Dow Chemicals, Midland, Mich.
(8) UCARE™ JR30M: Cationic HEC from Dow Chemicals, Midland, Mich.
(9) POLYSURF® 67: NT4C3594, Hydrophobically modified hydroxyethyl cellulose from Hercules, Inc.
(10) NATROSOL® 250M: Hydroxyethyl cellulose from Hercules, Inc., Wilmington, Del.
(11) NEXTON® 3082R: Hydrophobically modified hydroxyethyl cellulose from Hercules, Inc., Wilmington, Del.
(12) NATROSOL® 250HHR CS, Hydroxyethyl cellulose from Hercules, Inc., Wilmington, Del.

Examples 74-81

The polymer of the presently disclosed and/or claimed inventive concept(s) was incorporated into Colgate-Palmolive SOFTSOAP® Body Wash (Colgate-Palmolive Co., NY, N.Y.). The viscosity of the body wash increased (Example 77), and the clarity of the body wash was significantly better than for other commercial hydrophobic cellulose ethers or nonionic cellulose ethers (Examples 78-81).

The body wash was prepared by weighing 80 g commercial product into 4 oz. wide mouth glass jars, adding 20 g of a 1% polymer solution, capping and taping lid of jars with electrical tape, shaking the jars by hand to initially mix polymer, placing and securing the jars on tumbler using tape across jars and around jars on ends to prevent the jars from tumbling over the edge, tumbling the jars for 1.5 hours after which the jars were removed and tempered in a 25° C. bath overnight, and removing the jars from the bath the next day for observation and recordation of solution clarity, polymer solubility, and measuring the % T at 600 nm for the 24 hour samples. The samples were then stored at ambient conditions for two weeks after which the jars were again tempered in the bath overnight and observations and recordation of pH, viscosity, and % T were undertaken the next day.

TABLE 8

Examples Soft Soap - 0.2% Active

| Example # | Designation | Source | Composition | Initial (24 Hours) | | | |
|---|---|---|---|---|---|---|---|
| | | | | pH | Viscosity (cps) | Spindle #, Rpm | % T |
| 74 | Control - 100 g of SOFTSOAP ® - no water or polymer added | | | 7.19 | 5060.0 | #4, 30 | 97.7 |
| 75 | Control - 80 g of SOFTSOAP ® + 20 g of water added | | | 7.20 | 175.0 | #2, 30 | 97.1 |
| 76 | AQU D3673 | Experimental | $C_8$HMHEC | 7.14 | 337.0 | #2, 30 | 97.5 |
| 77 | AQU D3930 | invention | $C_{16}$HMHEC | 7.17 | 1628.0 | #3, 30 | 87.4 |
| 78 | POLYSURF ® 67 | Commercial | $C_{16}$HMHEC | 7.04 | 1332.0 | #3, 30 | 32.5 |
| 79 | NATROSOL ® Plus 330 | Commercial | $C_{16}$HMHEC | 7.09 | 783.0 | #2, 30 | 80.2 |
| 80 | NATROSOL ® 250HHR CS | Commercial | HEC | 7.11 | 249.0 | #2, 30 | 63.5 (polymer settled on bottom; shaken before % T taken) |
| 81 | NATROSOL ® 250M | Commercial | HEC | 7.11 | 236.0 | #2, 30 | 14.6 (polymer settled on bottom; shaken before % T taken) |

| Example # | Initial (24 Hours) | | 2 Weeks at Room Temp. | | | | |
|---|---|---|---|---|---|---|---|
| | Solution Clarity | pH | Viscosity (cps) | Spindle #, Rpm | % T | Solution Clarity | Polymer Solubility |
| 74 | Clear | 7.21 | 4600.0 | #4, 30 | 97.5 | Clear | |
| 75 | Clear | 7.23 | 173.0 | #2, 30 | 97.1 | Clear | |
| 76 | Clear | 7.20 | 331.0 | #2, 30 | 96.8 | Clear | Soluble |
| 77 | Very slight hazy | 7.21 | 1736.0 | #3, 30 | 87.5 | Very slight hazy | Soluble |
| 78 | Very hazy | 7.17 | 1380.0 | #3, 30 | 40.4 | Very hazy | Soluble |
| 79 | Hazy | 7.15 | 774.0 | #2, 30 | 81.2 | Hazy | Soluble |
| 80 | Hazy | 7.17 | 282.0 | #2, 30 | 74.1 | Hazy | Polymer gel layer on bottom |

TABLE 8-continued

| | | Examples Soft Soap - 0.2% Active | | | | | |
|---|---|---|---|---|---|---|---|
| 81 | Hazy | 7.18 | 282.0 | #2, 30 | 46.6 | Hazy | Polymer gel layer on bottom |

Examples 82-89

Incorporation of the polymer of the presently disclosed and/or claimed inventive concept(s) into LYSOL® All Purpose Cleaner (Reckitt Benckiser LLC, Parsippany, N.J.), increased the product viscosity relative to the control product containing no polymer (Compare Example 85 with 82 in Table 9). The polymer of the presently disclosed and/or claimed inventive concept(s) was slow to dissolve in the Lysol base, but this could be improved with formulation optimization.

The cleaner was prepared by weighing 80 g commercial product into 4 oz. wide mouth glass jars, adding 20 g of a 1% polymer solution to the jars, capping and taping lids of jars with electrical tape, shaking the jars by hand to initially mix polymer, placing and securing the jars on tumbler using tape across jars and around jars on ends to prevent the jars from tumbling over the edge, tumbling the jars for 1.5 hours after which the jars were removed and tempered in a 25° C. bath overnight, and removing the jars from the bath the next day for observation and recordation of solution clarity, polymer solubility, and measuring the % T at 600 nm for the 24 hour samples. The samples were then stored at ambient conditions for two weeks after which the jars were again tempered in the bath overnight and observations and recordation of pH, viscosity, and % T were undertaken the next day.

TABLE 9

Examples LYSOL ® All Purpose - 0.2% Active

| | | | | Initial (24 Hours) | | | | |
|---|---|---|---|---|---|---|---|---|
| Example # | Designation | Source | Composition | pH | Viscosity (cps) | Spindle #, Rpm | % T | Solution Clarity |
| 82 | Control - 100 g of LYSOL ® - no water or polymer added | | | 8.78 | 4.1 | #1, 60 | 99.4 | Clear |
| 83 | Control - 80 g of LYSOL ® + 20 g of water added | | | 8.75 | 3.4 | #1, 60 | 99.2 | Clear |
| 84 | AQU D3673 | Experimental | $C_8$HMHEC | 8.57 | 4.2 | #1, 60 | 99.6 | Clear |
| 85 | AQU D3930 | Polymer of invention | $C_{16}$HMHEC | 8.62 | 10.5 | #1, 60 | 99.0 | Clear |
| 86 | POLYSURF ® 67 | Commercial | $C_{16}$HMHEC | 8.51 | 10.1 | #1, 60 | 98.4 | Clear |
| 87 | NATROSOL ® Plus 330 | Commercial | $C_{16}$HMHEC | 8.47 | 6.2 | #1, 60 | 99.2 | Clear |
| 88 | NATROSOL ® 250HHR CS | Commercial | HEC | 8.55 | 21.5 | #1, 60 | 99.0 | Clear |
| 89 | NATROSOL ® 250M | Commercial | HEC | 8.49 | 9.7 | #1, 60 | 99.6 | Clear |

| | | 2 Weeks at Room Temp. | | | | | |
|---|---|---|---|---|---|---|---|
| Example # | Initial (24 Hours) Polymer Solubility | pH | Viscosity (cps) | Spindle #, Rpm | % T | Solution Clarity | Polymer Solubility |
| 82 | Control | 8.79 | 3.50 | #1, 60 | 99.3 | Clear | Control |
| 83 | Control | 8.79 | 3.20 | #1, 60 | 99.2 | Clear | Control |
| 84 | Soluble | 8.68 | 4.40 | #1, 60 | 99.7 | Clear | Soluble |
| 85 | Insoluble, undissolved polymer | 8.64 | 11.30 | #1, 60 | 98.5 | Clear | Soluble |
| 86 | Soluble | 8.58 | 12.40 | #1, 60 | 99.6 | Clear | Soluble |
| 87 | Soluble | 8.55 | 6.00 | #1, 60 | 99.8 | Clear | Soluble |
| 88 | Soluble | 8.62 | 19.10 | #1, 60 | 99.9 | Clear | Soluble |
| 89 | Soluble | 8.55 | 11.10 | #1, 60 | 99.9 | Clear | Soluble |

Examples 90-97

Incorporation of the polymer of the presently disclosed and/or claimed inventive concept(s) into Pine-sol® (The Clorox Company, Oakland, Calif.) more than doubled the viscosity of the product. (Compare viscosity for Example 93 with 90 in Table 10, for example.)

The cleaner was prepared by weighing 80 g commercial product into 4 oz. wide mouth glass jars, adding 20 g of a 1% polymer solution to the jars, capping and taping lids of jars with electrical tape, shaking the jars by hand to initially mix polymer, placing and securing the jars on tumbler using tape across jars and around jars on ends to prevent the jars from tumbling over the edge, tumbling the jars for 1.5 hours after which the jars were removed and tempered in a 25° C. bath overnight, and removing the jars from the bath the next day for observation and recordation of solution clarity, polymer solubility, and measuring the % T at 600 nm for the 24 hour samples. The samples were then stored at ambient conditions for two weeks after which the jars were again tempered in the bath overnight and observations and recordation of pH, viscosity, and % T were undertaken the next day.

Examples 98-105

Incorporation of the product of the invention into Clorox® (The Clorox Company, Oakland, Calif.) (compare Example 101 with 98) increased the viscosity of the product to a greater extent than any of the commercial hydrophobic or nonionic cellulose ethers in Table 11.

The cleaner was prepared by weighing 80 g commercial product into 4 oz. wide mouth glass jars, adding 20 g of a 1% polymer solution to the jars, capping and taping lids of jars with electrical tape, shaking the jars by hand to initially mix polymer, placing and securing the jars on tumbler using tape across jars and around jars on ends to prevent the jars from tumbling over the edge, tumbling the jars for 1.5 hours after which the jars were removed and tempered in a 25° C. bath overnight, and removing the jars from the bath the next day for observation and recordation of solution clarity, polymer solubility, and measuring the % T at 600 nm for the 24 hour samples. The samples were then stored at ambient conditions for two weeks after which the jars were again tempered in the bath overnight and observations and recordation of pH, viscosity, and % T were undertaken the next day.

TABLE 10

Examples PINE-SOL ® All Purpose - 0.2% Active

| Example # | Designation | Source | Composition | Initial (24 Hours) pH | Viscosity (cps) | Spindle # Rpm | % T | Solution Clarity |
|---|---|---|---|---|---|---|---|---|
| 90 | Control - 100 g of PINE-SQL ® - no water or polymer added | | | 10.1 | 43.0 | #2, 30 | 42.6 | Clear |
| 91 | Control - 80 g of PINE-SQL ® + 20 g of water added | | | 10.1 | 17.4 | #1, 30 | 50.5 | Clear |
| 92 | AQU D3673 | Experimental | $C_8$HMHEC | 9.93 | 30.0 | #2, 30 | 50.2 | Clear |
| 93 | AQU D3930 | Polymer of invention | $C_{16}$HMHEC | 9.87 | 84.0 | #2, 30 | 49.3 | Very slight hazy |
| 94 | POLYSURF ® 67 | Commercial | $C_{16}$HMHEC | 9.85 | 78.0 | #2, 30 | 49.5 | Clear |
| 95 | NATROSOL ® Plus 330 | Commercial | $C_{16}$HMHEC | 9.85 | 40.0 | #1, 30 | 49.2 | Clear |
| 96 | NATROSOL ® 250HHR CS | Commercial | HEC | 9.86 | 143.0 | #2, 30 | 49.9 | Clear |
| 97 | NATROSOL ® 250M | Commercial | HEC | 9.88 | 75.0 | #2, 30 | 50.1 | Clear |

| Example # | Initial (24 Hours) Polymer solubility | 2 Weeks at Room Temp. pH | Viscosity (cps) | Spindle # Rpm | % T | Solution Clarity | Polymer Solubility |
|---|---|---|---|---|---|---|---|
| 90 | Control | 10.02 | 38.5 | #2, 30 | 42.3 | Clear | Control |
| 91 | Control | 10.01 | 17.8 | #1, 30 | 50.5 | Clear | Control |
| 92 | Soluble | 9.88 | 29.0 | #2, 30 | 50.3 | Clear | Soluble |
| 93 | Soluble | 9.84 | 86.0 | #2, 30 | 48.4 | Very slight hazy | Soluble |
| 94 | Soluble | 9.83 | 80.0 | #2, 30 | 49.9 | Clear | Soluble |
| 95 | Soluble | 9.81 | 52.0 | #2, 30 | 49.8 | Clear | Soluble |
| 96 | Soluble | 9.85 | 136.0 | #2, 30 | 50.3 | Clear | Soluble |
| 97 | Soluble | 9.87 | 67.0 | #2, 30 | 50.5 | Clear | Soluble |

TABLE 11

| | | Examples CLOROX ® All Purpose - 0.2% Active | | | | | | |
|---|---|---|---|---|---|---|---|---|
| | | | | | Initial (24 Hours) | | | |
| Example # | Designation | Source | Composition | pH | Viscosity (cps) | Spindle #, Rpm | % T | Solution Clarity |
| 98 | Control - 100 g of CLOROL ® - no water or polymer added | | | 3.44 | 55.1 | #1, 60 | 96.5 | Clear |
| 99 | Control - 80 g of CLOROX ® + 20 g of water added | | | 3.51 | 10.6 | #1, 60 | 96.6 | Clear |
| 100 | AQU D3673 | Experimental | $C_8$HMHEC | 3.75 | 28.8 | #1, 60 | 95.6 | Clear |
| 101 | AQU D3930 | Polymer of invention | $C_{16}$HMHEC | 3.54 | 96.2 | #1, 30 | 95.8 | Clear |
| 102 | POLYSURF ® 67 | Commercial | $C_{16}$HMHEC | 3.61 | 81.2 | #1, 60 | 94.9 | Clear |
| 103 | NATROSOL ® Plus 330 | Commercial | $C_{16}$HMHEC | 3.63 | 31.9 | #1, 60 | 94.5 | Clear |
| 104 | NATROSOL ® 250HHR CS | Commercial | HEC | 3.55 | 79.6 | #1, 60 | 95.2 | Clear |
| 105 | NATROSOL ® 250M | Commercial | HEC | 3.56 | 34.1 | #1, 60 | 95.7 | Clear |

| | | 2 Weeks at Room Temp. | | | | | |
|---|---|---|---|---|---|---|---|
| Example # | Initial (24 Hours) Polymer solubility | pH | Viscosity (cps) | Spindle #, Rpm | % T | Solution Clarity | Polymer Solubility |
| 98 | Control | 3.48 | 48.4 | #1, 60 | 96.6 | Clear | Control |
| 99 | Control | 3.54 | 10.3 | #1, 60 | 96.2 | Clear | Control |
| 100 | Soluble | 3.75 | 25.4 | #1, 60 | 96.9 | Clear | Soluble |
| 101 | Soluble | 3.57 | 122.6 | #1, 30 | 95.5 | Clear | Soluble |
| 102 | Soluble | 3.50 | 87.7 | #1, 60 | 96.5 | Clear | Soluble |
| 103 | Soluble | 3.53 | 32.7 | #1, 60 | 95.4 | Clear | Soluble |
| 104 | Soluble | 3.48 | 69.2 | #1, 60 | 96.3 | Clear | Soluble |
| 105 | Soluble | 3.53 | 30.3 | #1, 60 | 96.4 | Clear | Soluble |

Effect of Multi-Tail and/or Sulfate-Free Surfactants on the Conditioning Properties of Nonionic Hydrophobically Modified Polysaccharide Compositions Examples 106-122 were prepared to illustrate the benefits of multi-tail surfactants and/or sulfate-free surfactants on the conditioning properties of compositions (e.g., shampoos) wherein the polymer therein is a nonionic hydrophobically modified polysaccharide. Examples 123-126 were prepared to illustrate the added benefit of sodium chloride on the conditioning performance of compositions (e.g., shampoos) containing sulfate-free surfactants alone or in combination with multi-tail surfactants, wherein the polymer in the conditioning composition is a nonionic hydrophobically modified polysaccharide. Examples 127-133 were prepared to illustrate the benefits of multi-tail surfactants on the conditioning properties of compositions (e.g. shampoos) wherein the concentration of hydrophobically modified polysaccharide varies from 0.3 weight percent to 1 weight percent.

A typical test method for measuring the conditioning performance of shampoo and conditioner applications consists of measuring the combability of wet hair that has been treated with a shampoo and/or conditioner. For Examples 106-125, the following Wet Comb Performance Measurement Test was used.

1. Wet Comb Performance Measurement Test

Performance was measured at a constant temperature and humidity (23° C. and 50% relative humidity). Equipment used was a Stable Micro Systems Texture Analyzer Xt2i. Each tress (standard 3.0 g and 26 cm long) was washed first with Sodium Laureth Sulfate (SLES) using the standard washing/rinsing procedure. Three tresses were used for each example: Each tress was shampooed with the agreed upon shampoo amount (0.3 g shampoo per 1 gram tress); after rinsing, the tress was loaded in the Texture Analyzer without any pre-combing; the Texture Analyzer was run under standard conditions through 200 mm distance from the upper part to the tip of the hair tress; a total of 5 tests were run on each tress; and the average wet comb energy was reported.

Examples 106-116

Examples 106-116 illustrate that multi-tail surfactants significantly improve the conditioning properties of nonionic hydrophobically modified polysaccharide compositions such that they provide similar or better conditioning benefits than compositions containing cationic polymers and/or silicones and/or emollients. Examples 106-109 are comparative examples. Examples 110-116 correspond to experimental samples, i.e., shampoo formulations, containing both a nonionic hydrophobically modified polysaccharide and at least one multi-tail surfactant.

Examples 106-107 (Comparative)

Examples 106 and 107 are comparative examples corresponding to two commercial shampoos in the marketplace. Example 106 corresponds to GARNIER® FRUCTIS® Nutri Repair shampoo (L'Oreal, Paris, FR) and Example 107 corresponds to DOVE® Damage Therapy Intensive Repair shampoo (Unilever, Englewood Cliffs, N.J.).

(Example 108) Comparative

Example 108 is a comparative shampoo formulation containing the cationic polymer Polyquaternium-10, commercially sold by Dow as UCARE™ JR 400. An ~100 g sample consists of:

| | |
|---|---|
| 73.42 g | Deionized Water |
| 0.50 g | Polyquaternium-10 (UCARE ™ JR400) |
| 17.34 g | Sodium Laureth Sulfate (TEXAPON ® N702 - 67.2% active) |
| 6.74 g | Cocamidopropyl Betain (TEGOBETAIN ® L7 - 29.68% active) |
| 0.50 g | Phenoxyethanol, Ethylhexylglycerin (EUXYL ® PE9010 - Schulke & Mayr) |
| As required | Citric Acid to Adjust pH |
| 1.50 g | Sodium Chloride (99.5%, Aldrich) |

(Example 109) Comparative

Example 109 is also a comparative shampoo formulation comprised of the same ingredients as the formulation presented in Example 108 except that the cationic polymer, Polyquaternium-10, is replaced with the nonionic HMHCE polymer of the presently disclosed and/or claimed inventive concept(s), AQU D3930, at a 0.7 weight percent concentration. The amount of deionized water was adjusted to account for the increased concentration of polymer in the sample.

Examples 110-112

Examples 110-112 are experimental formulations containing both nonionic hydrophobically modified polysaccharides and multi-tail surfactants. A ~100 g sample of the formulations consists of:

| | |
|---|---|
| Quantum Satis (q.s.) | Deionized Water |
| 0.70 g | Polymer of this invention or commercial polymer |
| 11.56 g | Sodium Laureth Sulfate (TEXAPON ® N702 - 69.2% active) |
| 6.74 g | Cocamidopropyl Betain (TEGOBETAIN ® L7 - 29.68% active) |
| 3.0 g | Multi-tail Surfactant(s) |
| 0.50 g | Phenoxyethanol, Ethylhexylglycerin (EUXYL ® PE9010 - Schulke & Mayr) |
| As required | Citric Acid or Sodium Hydroxide to adjust pH |
| 0.10-1.50 g | Sodium Chloride (99.5%, Aldrich) |

Examples 113-116

Examples 113-116 have the same basic experimental formulations as Examples 110-112, however, the concentration of multi-tail surfactant has been lowered to 2.5 weight percent. A ~100 g sample of the formulations consists of:

| | |
|---|---|
| Quantum Satis (q.s.) | Deionized Water |
| 0.70 g | Polymer of this invention or commercial polymer |
| 11.56 g | Sodium Laureth Sulfate (TEXAPON ® N702 - 69.2% active) |
| 6.74 g | Cocamidopropyl Betain (TEGOBETAIN ® L7 - 29.68% active) |
| 2.5 g | Multi-tail Surfactant(s) |
| 0.50 g | Phenoxyethanol, Ethylhexylglycerin (EUXYL ® PE9010 - Schulke & Mayr) |
| As required | Citric Acid or Sodium Hydroxide to adjust pH |
| 0.10-1.50 g | Sodium Chloride (99.5%, Aldrich) |

Wet Comb Performance Measurements on Highly Bleached Caucasian Virgin Brown Hair Treated with Compositions Containing Multi-Tail Surfactants—Table 12

The above-described wet comb performance test was performed on highly bleached Caucasian virgin brown hair for Examples 106-112. Prior to testing, Caucasian virgin brown hair was damaged by bleaching the hair for approximately 2.5 hours. The formulations and commercial shampoos corresponding to Examples 106-112 were added to individual tresses in amounts of 0.3 grams per gram of tress and then rinsed. After rinsing, the wet comb performance measurements were taken with a total of five tests run per tress. The results presented in Table 12 demonstrate that multi-tail surfactants significantly enhance the conditioning properties of compositions containing nonionic hydrophobically modified polysaccharide polymers.

TABLE 12

| Example # | Polymer (concentration) | Polymer Type | Multi-tail Surfactant (concentration) | Type of Multi-tail Surfactant | Wet combing (gf-mm/g) |
|---|---|---|---|---|---|
| 106 | GARNIER FRUCTIS ® Nutri Repair | | None | — | 420778 |
| 107 | DOVE ® Damage Therapy Intensive Repair | | None | — | 406384 |
| 108 | UCARE ™ JR400 (0.5 wt %) | Cationic | None | — | 378652 |
| 109 | AQU D3930 (0.7 wt %) | Nonionic | None | — | 416705 |
| 110 | AQU D3930 (0.7 wt %) | Nonionic | STEPANQUAT ® GA-90 (3 wt %) | Cationic | 239659 |
| 111 | AQU D3930 (0.7 wt %) | Nonionic | ARQUAT ® 2C-75 (3 wt %) | Cationic | 214502 |
| 112 | AQU D3930 (0.7 wt %) | Nonionic | AEROSOL ® OT (3 wt %) | Anionic | 245759 |

Description of Ingredients Listed in Table 12:
(1) GARNIER FRUCTIS® Nutri Repair: Commercial shampoo, L'Oreal, Paris, FR.
(2) DOVE® Damage Therapy Intensive Repair: Commercial shampoo, Unilever, Englewood Cliffs, N.J.
(3) UCARE™ JR400: Cationic HEC, Polyquaternium-10, from Dow Chemicals, Midland, Mich.
(4) AQU D3930: Polymer of this invention, C16 hydrophobically modified hydroxyethyl cellulose from Hercules, Inc. 1.1 wt % cetyl, hydroxyethyl molar substitution (HEMS) 4.0.
(5) STEPANQUAT® GA-90: Cationic multi-tail surfactant, Dipalmitoylethyl hydroxyethylmonium methosulfate, from Stepan Compan, Northfield, Ill.
(6) ARQUAT® 2C-75: Cationic multi-tail surfactant, dicoco dimethylammonium chloride, from Akzo-Nobel.
(7) AEROSOL® OT: Anionic multi-tail surfactant, sodium dioctyl sulphosuccinate, from Cytec Industries Inc., West Paterson, N.J.

Wet Comb Performance Measurements on Mildly Bleached Chinese Hair with Compositions Containing Multi-Tail Surfactants—Table 13

The above-described wet comb performance test was also performed on mildly bleached Chinese hair for Examples 114-116 and Comparative Examples 108-109. Prior to testing, the Chinese hair was damaged by bleaching the hair for approximately 1 hour. The shampoo formulations for Examples 108-109 and 114-116 were added to individual tresses in amounts of 0.3 grams per gram of tress and then rinsed. After rinsing, the wet comb performance measurements were taken with a total of five tests run per tress. The results presented in Table 13 also indicate a significant improvement in conditioning properties due to the addition of multi-tail surfactants.

| q.s. | Deionized Water |
| 0.10 g | Disodium EDTA (EDETA ® BD - BASF) |
| 0.70-1.0 g | Polymer of this invention or commercial polymer |
| 10.00 g | Sodium Lauroyl Sarcosinate (MEDIALAN ® LD, 30% active - Clariant) |
| 6.00 g | Sodium Lauroamphoacetate (JEETERIC ® LM-M30, 41% active - Jeen International) |

TABLE 13

| Example # | Polymer (Concentration) | Polymer Type | Multi-tail Surfactant (Concentration) | Type of Multi-tail Surfactant | Wet Combing (gf-mm/g) |
|---|---|---|---|---|---|
| 108 | UCARE ™ JR 400 (0.5 wt %) | Cationic | None | — | 380171 |
| 109 | AQU D3930 (0.7 wt %) | Nonionic | None | — | 180487 |
| 113 | AQU D3930 (0.7 wt %) | Nonionic | STEPANTEX ® DC 90 (2.5 wt %) | Cationic | 62081 |
| 114 | AQU D3930 (0.7 wt %) | Nonionic | STEPANQUAT ® GA-90 (2.5 wt %) | Cationic | 54229 |
| 115 | AQU D3930 (0.7 wt %) | Nonionic | ARQUAT ® 2C-75 (2.5 wt %) | Cationic | 44974 |
| 116 | AQU D3930 (0.7 wt %) | Nonionic | AEROSOL ® OT (2.5 wt %) | Anionic | 46395 |

Description of Ingredients Listed in Table 13:
(1) UCARE™ JR400: Cationic HEC, Polyquaternium-10, from Dow Chemicals, Midland, Mich.
(2) AQU D3930: Polymer of this invention, C16 hydrophobically modified hydroxyethyl cellulose from Hercules, Inc., 1.1 wt % cetyl, hydroxyethyl molar substitution (HEMS) 4.0.
(3) STEPANTEX® DC 90: Cationic multi-tail surfactant, dialkyl ammonium methosulfate, from Stepan Company, Northfield, Ill.
(4) STEPANQUAT® GA-90: Cationic multi-tail surfactant, Dipalmitoylethyl hydroxyethylmonium methosulfate, from Stepan Company, Northfield, Ill.
(5) ARQUAT® 2C-75: Cationic multi-tail surfactant, dicoco dimethylammonium chloride, from Akzo-Nobel.
(6) AEROSOL® OT: Anionic multi-tail surfactant, sodium dioctyl sulphosuccinate, from Cytec Industries Inc., West Paterson, N.J.

Wet Comb Performance Measurements on Highly Bleached Caucasian Virgin Brown Hair Treated with Sulfate-Free Shampoos—Table 14

The following examples, Examples 117-119, illustrate that limiting nonionic hydrophobically modified polysaccharide compositions to include surfactants consisting only of sulfate-free surfactants (as opposed to sulfate-containing surfactants) also improves the conditioning properties of the compositions such that they provide similar or better conditioning benefits than compositions containing cationic polymers and/or silicones and/or emollients. Examples 106-108 include sodium laureth sulfate, a sulfate-containing surfactant, in their formulations and are therefore used as comparative examples with respect to Examples 117-119.

Example 117 is an experimental formulation containing a nonionic hydrophobically modified polysaccharide wherein the surfactants contained therein are limited solely to (single tail) sulfate-free surfactants. A ~100 g sample of the formulation consists of:

| 15.00 g | Coamidopropyl Betain (AMPHOSOL ® CG-K, 30% active - Stepan Company) |
| 2.00 g | Decyl glucoside (PLANTACARE ® 2000, 54% active - Cognis) |
| 0.20 g | Methylisothiazolinone and Phenethyl alcohol and PPG-2-Methyl Ether (OPTIPHEN ® MIT Plus - Ashland Specialty Ingredients) |
| As required | Citric acid to adjust pH |
| None-3.0 g | Sodium Chloride (99.5%, Aldrich) |

Examples 118-119 are additional experimental formulations containing nonionic hydrophobically modified polysaccharides wherein the surfactants are limited solely to (single tail) sulfate-free surfactants. A ~100 g sample of the formulations consists of:

| q.s. | Deionized Water |
| 0.10 g | Disodium EDTA (EDETA ® BD - BASF) |
| 0.70-1.0 g | Polymer of this invention or commercial polymer |
| 16.67 g | Sodium Lauroyl Sarcosinate (MEDIALAN ® LD, 30% active - Clariant) |
| 12.20 g | Sodium Lauroamphoacetate (JEETERIC ® LM-M30, 41% active - Jeen International) |
| 7.41 g | Decyl glucoside (PLANTACARE ® 2000, 54% active - Cognis) |
| 0.20 g | Methylisothiazolinone and Phenethyl alcohol and PPG-2-Methyl Ether (OPTIPHEN ® MIT Plus - Ashland Specialty Ingredients) |
| As required | Citric acid to adjust pH |
| None-1.0 g | Sodium Chloride (99.5%, Aldrich) |

The above-described wet comb performance test was performed on highly bleached Caucasian virgin brown hair for Examples 117-119 and Comparative Examples 106-108. Prior to testing, the Caucasian virgin brown hair was damaged by bleaching the hair for approximately 2.5 hours. The formulations and commercial shampoos corresponding to Examples 106-108 and 117-119 were added to individual tresses in amounts of 0.3 grams per gram of tress and then rinsed. After rinsing, the wet comb performance measurements were taken with a total of five tests run per tress. The results are presented in Table 14.

TABLE 14

| Example # | Polymer (concentration) | Polymer Type | NaCl Concentration | Wet Combing (gf-mm/g) |
|---|---|---|---|---|
| 106 | GARNIER FRUCTIS ® Nutri Repair | | | 420778 |
| 107 | DOVE ® Damage Repair Therapy Intensive Repair | | | 406384 |
| 108 | UCARE ™ JR400 (0.5 wt %) | Cationic | 1.5 wt % | 378652 |
| 117 | AQU D3930 (0.7 wt %) | Nonionic | 3 wt % | 251791 |
| 118 | AQU D3930 (1 wt %) | Nonionic | 0.2 wt % | 363231 |
| 119 | NATROSOL ® Plus 330 (1 wt %) | Nonionic | 1 wt % | 378276 |

Description of Ingredients Listed in Table 14:
(1) GARNIER FRUCTIS® Nutri Repair: Commercial Shampoo, L'Oreal, Paris, FR.
(2) DOVE® Damage Therapy Intensive Repair: Commercial Shampoo, Unilever, Englewood Cliffs, N.J.
(3) UCARE™ JR400: Cationic HEC, Polyquaternium-10, from Dow Chemicals, Midland, Mich.
(4) AQU D3930: Polymer of this invention, C16 hydrophobically modified hydroxyethyl cellulose from Hercules, Inc., 1.1 wt % cetyl, hydroxyethyl molar substitution (HEMS) 4.0.
(5) NATROSOL® Plus 330: Hydroxyethyl cellulose from Hercules, Inc.

Wet Comb Performance Measurements on Highly Bleached Caucasian Virgin Brown Hair Treated with Shampoo Compositions Containing Multi-Tail Surfactants and Single Tail Sulfate-Free Surfactants—Table 15

Examples 120-122 illustrate that the addition of multi-tail surfactants (whether sulfate-free or not) to nonionic hydrophobically modified polysaccharide compositions containing sulfate-free single tail surfactants provides similar or better conditioning benefits than those compositions containing cationic polymers and/or silicones and/or emollients. Examples 106-108 and Example 117 are comparative examples and are described above. A ~100 g sample of the formulation for Examples 120-122 consists of:

| q.s. | Deionized Water |
|---|---|
| 0.10 g | Disodium EDTA (EDETA ® BD - BASF) |
| 0.70-1.0 g | Polymer of this invention or commercial polymer |
| 10.00 g | Sodium Lauroyl Sarcosinate (MEDIALAN ® LD, 30% active - Clariant) |
| 6.00 g | Sodium Lauroamphoacetate (JEETERIC ® LM-M30, 41% active - Jeen International) |
| 15.00 g | Coamidopropyl Betain (AMPHOSOL ® CG-K, 30% active - Stepan Company) |
| 2.00 g | Decyl glucoside (PLANTACARE ® 2000, 54% active - Cognis) |
| 3.00 g | Multi-tail Surfactant(s) |
| 0.20 g | Methylisothiazolinone and Phenethyl alcohol and PPG-2-Methyl Ether (OPTIPHEN ® MIT Plus - Ashland Specialty Ingredients) |
| As required | Citric acid to adjust pH |
| None-3.0 g | Sodium Chloride (99.5% Aldrich) |

The above-described wet comb performance test was performed on highly bleached Caucasian virgin brown hair for Examples 120-122 and Comparative Examples 106-108 and 117. Prior to testing, the Caucasian virgin brown hair was damaged by bleaching the hair for approximately 2.5 hours. The formulations and commercial shampoos corresponding to Examples 106-108, 117, and 120-122 were added to individual tresses in amounts of 0.3 grams per gram of tress and then rinsed. After rinsing, the wet comb performance measurements were taken with a total of five tests run per tress. The results are presented in Table 15.

TABLE 15

| Example # | Polymer (concentration) | Polymer Type | Concentration of NaCl | Multi-tail Surfactant (concentration) | Type of Multi-tail Surfactant | Wet Combing (gf-mm/g) |
|---|---|---|---|---|---|---|
| 106 | GARNIER FRUCTIS ® Nutri Repair | | | None | N/A | 420778 |
| 107 | DOVE ® Damage Repair Therapy Intensive Repair | | | None | N/A | 406778 |
| 108 | UCARE ™ JR400 (0.5 wt %) | Cationic | 1.5 wt % | None | N/A | 378652 |
| 117 | AQU D3930 (0.7 wt %) | Nonionic | 3 wt % | None | N/A | 251791 |
| 120 | AQU D3930 (0.7 wt %) | Nonionic | 0.1 wt % | STEPANTEX ® DC 90 (3 wt %) | Cationic | 371131 |
| 121 | AQU D3930 (0.7 wt %) | Nonionic | 0.1 wt % | STEPANQUAT ® GA-90 (3 wt %) | Cationic | 284344 |
| 122 | AQU D3930 (0.7 wt %) | Nonionic | 0.1 wt % | ARQUAT ® 2C-75 (3 wt %) | Cationic | 165465 |

Description of Ingredients Listed in Table 15:
(1) GARNIER FRUCTIS® Nutri Repair: Commercial Shampoo L'Oreal, Paris, FR.
(2) DOVE® Damage Therapy Intensive Repair: Commercial Shampoo, Unilever, Englewood Cliffs, N.J.
(3) UCARE™ JR400: Cationic HEC, Polyquaternium-10, from Dow Chemicals, Midland, Mich.
(4) AQU D3930: Polymer of this invention, C16 hydrophobically modified hydroxyethyl cellulose from Hercules, Inc. 1.1 wt % cetyl, hydroxyethyl molar substitution (HEMS) 4.0.
(5) STEPANTEX® DC 90: Cationic multi-tail surfactant, dialkyl ammonium methosulfate, from Stepan Company, Northfield, Ill.
(6) STEPANQUAT® GA-90: Cationic multi-tail surfactant, Dipalmitoylethyl hydroxyethylmonium methosulfate, from Stepan Company, Northfield, Ill.
(7) ARQUAT® 2C-75: Cationic multi-tail surfactant, dicoco dimethylammonium chloride, from Akzo-Nobel.

Wet Comb Performance Measurements on Highly Bleached Caucasian Virgin Brown Hair Treated with Shampoo Compositions Containing Varying Levels of Sodium Chloride and Multi-Tail Surfactants and/or Single Tail Sulfate-Free Surfactants—Table 16

Examples 123-126 illustrate the crucial role of sodium chloride on the performance of sulfate-free nonionic hydrophobically modified shampoos alone or in combination with multi-tail surfactants. A ~100 g sample of the formulation for Examples 123-126 consists of:

| | |
|---|---|
| q.s. | Deionized Water |
| 0.10 g | Disodium EDTA (EDETA ® BD - BASF) |
| 0.70-1.0 g | Polymer of this invention or commercial polymer |
| 16.67 g | Sodium Lauroyl Sarcosinate (MEDIALAN ® LD, 30% active - Clariant) |
| 12.20 g | Sodium Lauroamphoacetate (JEETERIC ® LM-M30, 41% active - Jeen International) |
| 7.41 g | Decyl glucoside (PLANTACARE ® 2000, 54% active - Cognis) |
| 0.0-3.0 g | Multi-tail surfactant(s) |
| 0.20 g | Methylisothiazolinone and Phenethyl alcohol and PPG-2-Methyl Ether (OPTIPHEN ® MIT Plus - Ashland Specialty Ingredients) |
| As required | Citric acid to adjust pH |
| None-1.0 g | Sodium Chloride (99.5%, Aldrich) |

The above-described wet comb performance test was performed on highly bleached Caucasian virgin brown hair for Examples 123-126. Prior to testing, the Caucasian virgin brown hair was damaged by bleaching the hair for approximately 2.5 hours. The formulations were added to individual tresses in amounts of 0.3 grams per gram of tress and then rinsed. After rinsing, the wet comb performance measurements were taken with a total of five tests run per tress. The results are presented in Table 16.

Wet Comb Performance Measurements on Non-Bleached Caucasian Virgin Brown Hair Treated with Shampoo Compositions Containing Varying Levels of Nonionic Hydrophobically Modified Polysaccharide and Multi-Tail Surfactants—Table 17

Examples 127-133 illustrate that multi-tail surfactants significantly improve the conditioning properties of compositions containing a range of concentrations of nonionic hydrophobically modified polysaccharides such that they provide similar or better conditioning benefits than compositions containing cationic polymers and/or silicones and/or emollients. Examples 127-130 are comparative examples. Examples 131-133 correspond to experimental samples containing both a nonionic hydrophobically modified polysaccharide and at least one multi-tail surfactant.

Comparative Examples 127 and 128 correspond to the commercial shampoos GARNIER FRUCTIS® Nutri Repair (L'Oreal, Paris, FR) and DOVE® Damage Therapy Intensive Repair (Unilever, Englewood Cliffs, N.J.).

Comparative Examples 129-130 are shampoo formulations without multi-tail surfactants. A ~100 g sample of the formulations for Examples 129-130 consists of:

| | |
|---|---|
| q.s. | Deionized Water |
| 0.50-0.70 g | Polymer of this invention or commercial polymer |
| 17.34 g | Sodium Laureth Sulfate (TEXAPON ® N702 - 69.2% active) |
| 6.74 g | Cocamidopropyl Betain (TEGOBETAIN ® L7 - 29.68% active) |
| 0.50 g | Phenoxyethanol, Ethylhexylglycerin (EUXYL ® PE9010 - Schulke & Mayr) |
| As required | Citric acid to adjust pH |
| 0.10-1.50 g | Sodium Chloride (99.5%, Aldrich) |

TABLE 16

| Example # | Polymer (Concentration) | Polymer Type | Concentration of NaCl | Multi-tail Surfactant (Concentration) | Type of Multi-tail Surfactant | Wet Combing (gf-mm/g) |
|---|---|---|---|---|---|---|
| 123 | AQU D3930 (1 wt %) | Nonionic | — | None | — | 625635 |
| 124 | AQU D3930 (1 wt %) | Nonionic | 0.2 wt % | None | — | 363231 |
| 125 | NATROSOL ® Plus 330 (1 wt %) | Nonionic | — | Aerosol ® OT (2.5 wt %) | Anionic | 390873 |
| 126 | NATROSOL ® Plus 330 (1 wt %) | Nonionic | 1 wt % | Aerosol ® OT (2.5 wt %) | Anionic | 35976 |

Description of Ingredients Listed in Table 16:

(1) AQU D3930: Polymer of this invention, C16 hydrophobically modified hydroxyethyl cellulose from Hercules, Inc., 1.1 wt % cetyl, hydroxyethyl molar substitution (HEMS) 4.0.

(2) NATROSOL® Plus 330: Hydroxyethyl cellulose from Hercules, Inc.

(3) AEROSOL® OT: Anionic multi-tail surfactant, sodium dioctyl sulphosuccinate, from Cytec Industries Inc., West Paterson, N.J.

Examples 131-133 are shampoo formulations having a range of hydrophobically modified polysaccharide concentrations and include multi-tail surfactants. A ~100 g sample of the formulations for Examples 131-133 consists of:

| | |
|---|---|
| q.s. | Deionized Water |
| 0.30-1.0 g | Polymer of this invention or commercial polymer |
| 11.56 g | Sodium Laureth Sulfate (TEXAPON ® N702 - 69.2% active) |

-continued

| 6.74 g | Cocamidopropyl Betain (TEGOBETAIN® L7 - 29.68% active) |
| 0.0-3.0 g | Multi-tail Surfactant(s) |
| 0.50 g | Phenoxyethanol, Ethylhexylglycerin (EUXYL® PE9010 - Schulke & Mayr) |
| As required | Citric acid or Sodium Hydroxide to adjust pH |
| 0.10-1.50 g | Sodium Chloride (99.5%, Aldrich) |

The above-described wet comb performance test was performed on Caucasian virgin brown hair for Examples 127-133. The Caucasian virgin brown hair was not bleached or damaged prior to testing. The formulations and commercial shampoos were added to individual tresses in amounts of 0.3 grams per gram of tress and then rinsed. After rinsing, the wet comb performance measurements were taken with a total of five tests run per tress. The results are presented in Table 17.

TABLE 17

| Example # | Polymer (Concentration) | Polymer Type | Multi-tail Surfactant (Concentration) | Type of Multi-tail Surfactant | Wet Combing (gf-mm/g) |
|---|---|---|---|---|---|
| 127 | GARNIER FRUCTIS® Nutri Repair Shampoo | | None | N/A | 96350 |
| 128 | DOVE® Damage Therapy Intensive Repair Shampoo | | None | N/A | 98189 |
| 129 | UCARE™ JR400 (0.5 wt %) | Cationic | None | N/A | 76689 |
| 130 | AQU D3930 (0.7 wt %) | Nonionic | None | N/A | 244406 |
| 131 | AQU D3930 (0.3 wt %) | Nonionic | AEROSOL® OT (3 wt %) | Anionic | 129849 |
| 132 | AQU D3930 (0.7 wt %) | Nonionic | AEROSOL® OT (3 wt %) | Anionic | 103353 |
| 133 | AQU D3930 (1 wt %) | Nonionic | AEROSOL® OT (3 wt %) | Anionic | 83373 |

Description of Ingredients Listed in Table 17:
(1) GARNIER FRUCTIS® Nutri Repair: Commercial Shampoo, L'Oreal, Paris, FR.
(2) DOVE® Damage Therapy Intensive Repair: Commercial Shampoo Unilever, Englewood Cliffs, N.J.
(3) UCARE™ JR400: Cationic HEC, Polyquaternium-10, from Dow Chemicals, Midland, Mich.
(4) AQU D3930: Polymer of this invention, C16 hydrophobically modified hydroxyethyl cellulose from Hercules, Inc., 1.1 wt % cetyl, hydroxyethyl molar substitution (HEMS) 4.0.
(5) AEROSOL® OT: Anionic multi-tail surfactant, sodium dioctyl sulphosuccinate, from Cytec Industries Inc., West Paterson, N.J.

What is claimed:
1. A composition for conditioning hair comprising an aqueous solution, comprising:
   a. at least one sulfate-free multi-tail surfactant and at least one sulfate-free single-tail surfactant, wherein the at least one sulfate-free multi-tail surfactant has at least two hydrophobic alkyl chains, wherein each hydrophobic alkyl chain has from 8-12 carbons;
   b. at least one active ingredient;
   c. a nonionic hydrophobically modified cellulose ether having a weight average molecular weight of from 100,000 to 2,000,000 that is hydrophobically substituted, and
   d. sodium chloride;
   wherein the composition is free of sulfate-containing surfactants, and
   wherein the amount of hydrophobic substitution of the nonionic hydrophobically modified cellulose ether is in a range from a lower limit of 0.8 weight percent to an upper limit rendering the nonionic hydrophobically modified cellulose ether soluble in a five weight percent solution of surfactant, and at least one of (1) less than 0.5 percent by weight soluble in water, and (2) less than 0.05 percent by weight soluble in a one percent surfactant solution, wherein upon diluting the aqueous solution with water, the aqueous solution undergoes syneresis, whereby the nonionic hydrophobically modified cellulose ether separates from the aqueous solution and deposits upon the functional system substrate.

2. The composition of claim 1, wherein the upper limit of the weight average molecular weight of the nonionic hydrophobically modified cellulose ether is selected from the group consisting of 1,500,000 and 1,000,000.

3. The composition of claim 1, wherein the lower limit of the weight average molecular weight of the nonionic hydrophobically modified cellulose ether is selected from the group consisting of 200,000 and 600,000.

4. The composition of claim 1, wherein the nonionic hydrophobically modified cellulose ether has a hydrophobic moiety selected from the group consisting of alkyl, aryl, alkyl aryl, aryl alkyl, and combinations thereof.

5. The composition of claim 4, wherein the hydrophobic moiety is an alkyl having less than or equal to 12 carbons.

6. The composition of claim 4, wherein the hydrophobic moiety is selected from the group consisting of cetyl, octyl, and butyl.

7. The composition of claim 4, wherein the hydrophobic moiety is 3-alkoxy-2-hydroxypropyl.

8. The composition of claim 1, wherein the nonionic hydrophobically modified cellulose ether has a backbone selected from the group consisting of hydroxyethylcellulose, hydroxypropylcellulose, ethyl hydroxyethylcellulose, methyl hydroxyethylcellulose, hydroxypropylmethylcellulose, hydroxypropylhydroxyethylcellulose, ethyl hydroxypropylcellulose, and methylcellulose.

9. The composition of claim 4, wherein the nonionic hydrophobically modified cellulose ether has a hydrophobic moiety attached to the backbone via an ether, ester, or urethane linkage.

10. The composition of claim 1, wherein the at least one sulfate-free multi-tail surfactant is selected from the group consisting of anionic, nonionic, zwitterionic, and amphoteric multi-tail surfactants.

11. The composition of claim 10, wherein the at least one sulfate-free multi-tail surfactant is present in an amount ranging from 0.01 to 50 weight percent.

12. The composition of claim 1, wherein the at least one sulfate-free single-tail surfactant is selected from the group consisting of anionic, nonionic, zwitterionic, and amphoteric surfactants.

13. The composition of claim 12, wherein the at least one sulfate-free single-tail surfactant is present in an amount ranging from 0.01 to 50 weight percent.

14. The composition of claim 1, wherein the aqueous solution further comprises a solvent selected from the group consisting of water-lower alkanols mixtures and polyhydric alcohols having 3 to 6 carbons and 2 to 6 hydroxyl groups.

15. The composition of claim 1, wherein the sodium chloride is present in an amount ranging from 0.1 to 5 weight percent.

16. The composition of claim 1, wherein the at least one active ingredient is selected from the group consisting of perfumes, skin colorants, emollients, moisturizers, deodorants, antiperspirants, moisturizing agents, cleansers, sunscreens, hair treatment agents, conditioning agents, beauty aids, and personal care agents.

17. The composition of claim 16, wherein the composition for conditioning hair has a compositional form selected from the group consisting of oil-in-water emulsions, water-in-oil emulsions, solutions, slurries, dispersions, suspensions, and combinations thereof.

18. The composition of claim 10, wherein the at least one sulfate-free multi-tail surfactant is selected from dioctyl sulphosuccinates and dicoco dimethylammonium chloride.

* * * * *